US008401257B2

(12) United States Patent
Izatt et al.

(10) Patent No.: US 8,401,257 B2
(45) Date of Patent: Mar. 19, 2013

(54) METHODS, SYSTEMS AND COMPUTER PROGRAM PRODUCTS FOR PROCESSING IMAGES GENERATED USING FOURIER DOMAIN OPTICAL COHERENCE TOMOGRAPHY (FDOCT)

(75) Inventors: Joseph A. Izatt, Raleigh, NC (US); Eric L. Buckland, Hickory, NC (US); Bennett R. Groshong, Raleigh, NC (US); Bradley A. Bower, Hillsborough, NC (US)

(73) Assignee: Bioptigen, Inc., Durham, NC (US)

( * ) Notice: Subject to any disclaimer, the term of this patent is extended or adjusted under 35 U.S.C. 154(b) by 1098 days.

(21) Appl. No.: 12/016,352

(22) Filed: Jan. 18, 2008

(65) Prior Publication Data

US 2008/0181477 A1    Jul. 31, 2008

Related U.S. Application Data

(60) Provisional application No. 60/881,201, filed on Jan. 19, 2007.

(51) Int. Cl.
*G06K 9/20* (2006.01)
(52) U.S. Cl. ........ 382/128; 382/131; 382/132; 382/191; 382/276; 382/280
(58) Field of Classification Search .................. 382/128, 382/131, 132, 276, 280, 191
See application file for complete search history.

(56) References Cited

U.S. PATENT DOCUMENTS

| 5,150,421 A | 9/1992 | Morishita et al. |
| 5,204,627 A | 4/1993 | Mistretta et al. |
| 5,226,113 A | 7/1993 | Cline et al. |
| 5,233,299 A | 8/1993 | Souza et al. |
| 5,297,551 A | 3/1994 | Margosian et al. |
| 5,368,033 A | 11/1994 | Moshfeghi |
| 5,760,781 A | 6/1998 | Kaufman et al. |
| 6,102,864 A | 8/2000 | Hatfield et al. |
| 6,436,049 B1 | 8/2002 | Kamiyama et al. |
| 6,519,354 B1 | 2/2003 | Oshio |
| 6,554,504 B2 | 4/2003 | Cook et al. |
| 6,904,163 B1 | 6/2005 | Fujimura et al. |
| 7,020,318 B2 | 3/2006 | Oshio et al. |

(Continued)

FOREIGN PATENT DOCUMENTS

WO    WO 2005/117534 A2    12/2005

OTHER PUBLICATIONS

Notification of Transmittal of the International Search Report and the Written Opinion of the International Searching Authority, or the Declaration, PCT/US2008/000673; Nov. 17, 2008.

(Continued)

*Primary Examiner* — David A Vanore
(74) *Attorney, Agent, or Firm* — Myers Bigel Sibley & Sajovec

(57) ABSTRACT

Methods, systems and computer program products for managing frequency domain optical coherence tomography (FDOCT) image resolution. A spectrum used to acquire an image of a subject is calibrated and default dispersion correction parameters are set. Default dispersion management parameters associated with a region of the image of the subject are also set. The image of the subject is acquires after setting the default dispersion correction parameters and the default dispersion management parameters. A quality of the acquired image is compared to a quality metric for the acquired image. The dispersion correction parameters are adjusted if the quality of the acquired image does not meet or exceed the quality metric for the acquired image. The acquired image is reprocesses based on the adjusted dispersion correction parameters. The steps of comparing, adjusting and reprocessing are repeated until the acquired image meets or exceeds the quality metric for the acquired image.

16 Claims, 20 Drawing Sheets

U.S. PATENT DOCUMENTS

| | | | |
|---|---|---|---|
| 7,039,643 | B2 | 5/2006 | Sena et al. |
| 7,170,517 | B2 | 1/2007 | Raman et al. |
| 7,277,880 | B1 | 10/2007 | Sekine et al. |
| 7,277,903 | B2 | 10/2007 | Petrocelli |
| 7,298,451 | B2 | 11/2007 | Fancher |
| 7,301,644 | B2 | 11/2007 | Knighton et al. |
| 7,310,651 | B2 | 12/2007 | Dave et al. |
| 7,505,142 | B2 | 3/2009 | Knighton et al. |
| 2005/0018201 | A1 | 1/2005 | De Boer et al. |
| 2005/0171438 | A1* | 8/2005 | Chen et al. ............... 600/476 |
| 2006/0055936 | A1* | 3/2006 | Yun et al. ............... 356/479 |
| 2006/0171503 | A1 | 8/2006 | O'Hara et al. |
| 2007/0002327 | A1 | 1/2007 | Zhou et al. |
| 2007/0025642 | A1 | 2/2007 | Buckland et al. |
| 2007/0258094 | A1 | 11/2007 | Izatt et al. |
| 2007/0291277 | A1 | 12/2007 | Everett et al. |

OTHER PUBLICATIONS

Lu, Chih-Wei et al., "Software Dispersion Compensation in Optical Coherence Tomography," Cleo/Pacific Rim 2003—The 5$^{th}$ Pacific Rim Conference on Lasers and Electro-Otics, Dec. 15-29, 2003, Piscataway, NJ USA, IEEE, vol. 1, p. 127.

PCT International Search Report for International Application No. PCT/US2008/000673; Jul. 23, 2008.

XP-002457949 Wojtkowski M. et al. Ultrahigh-resolution, high-speed, Fourier domain optical coherence tomography and methods for dispersion compensation. Optics Express vol. 12(11) pp. 2404-2422, 2004.

XP-002373647 Cense B. et al. Ultrahigh-resolution, high-speed, retinal imaging using spectral-domain optical coherence tomography. Optics Express vol. 12(11) pp. 2435-2447, 2004.

XP-002486944 Choi, D. et al. Numerical Compensation of Dispersion Mismatch in Discretely Swept Optical-Frequency-Domain-Reflectometry Optical Coherence Tomography. Japanese Journal of Applied Physics vol. 45 (6) pp. 6022-6027, 2006.

XP-00258282 Leitgeb RA et al. Ultrahigh resolution Fourier domain optical coherence tomography. Optics Express vol. 12(10) pp. 2156-2164, 2004.

W1E-(12)-4 Lu Chih-Wei et al. Software Dispersion Compensation in Optical Coherence Tomography, 2004.

XP-002486944 Choi, D. et al. Numerical Compensation of Dispersion Mismatch in Discretely Swept Optical-Frequency-Domain-Reflectometry Optical Coherence Tomography. Japanese Journal of Applied Physics vol. 45 (7) pp. 6022-6027, 2006.

Bruckner, Stefan, "Introduction to Scientific Visualization," Simon Fraser University/Vienna University of Technology, Applicants' Admitted Prior Art, 17 pages, 2010.

Kaufman et al., "Real-Time Volume Rendering," to appear in the International Journal of Imaging Systems and Technology, special issue on 3D Imaging, Center for Visual Computing (CVC) and Department of Computer Science, State University of New York at Stony Brook, Applicants' Admitted Prior Art, 9 pages, 2010.

Heidrich et al., "Interactive Maximum Projection Volume Rendering," Sixth IEEE Visualization 1995 (VIS '95), Oct. 29-Nov. 3, 1995, 1 page.

Totsuka et al., "Frequency Domain Volume Rendering," Sony Corporation, Applicants' Admitted Prior Art, pp. 271-278, 2010.

Hylton, Nola M., "Angiographic display method for flow-enhanced MRI", Abstract, Publication Date Jun. 1992, http://adsabs.harvard.edu/abs/1992SPIE.1652.107H, 2 pages.

* cited by examiner

Figure 20
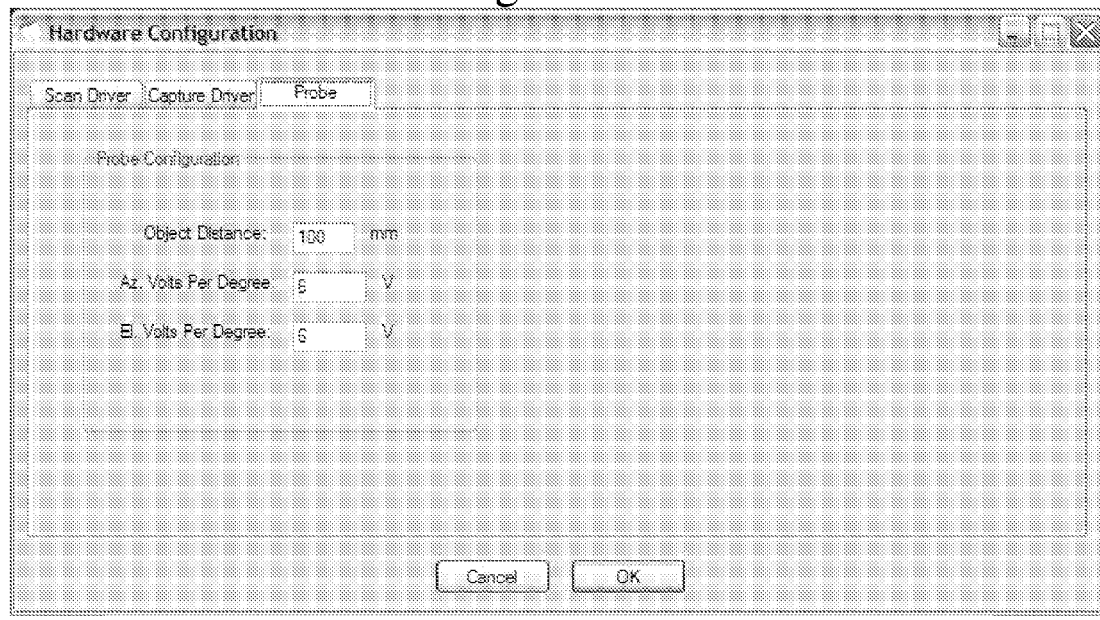
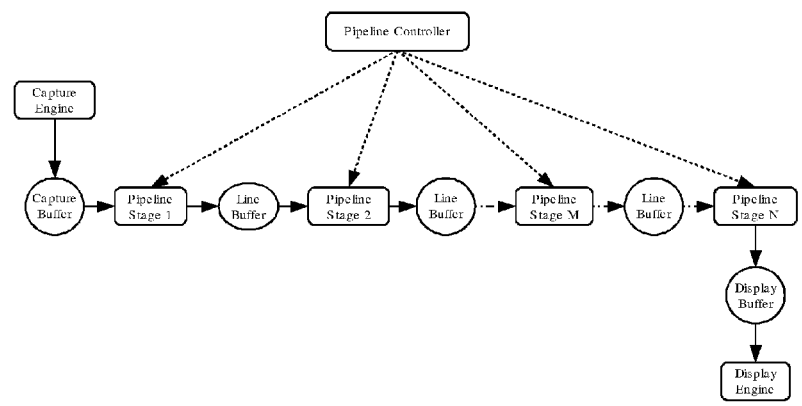
Figure 21

US 8,401,257 B2

METHODS, SYSTEMS AND COMPUTER PROGRAM PRODUCTS FOR PROCESSING IMAGES GENERATED USING FOURIER DOMAIN OPTICAL COHERENCE TOMOGRAPHY (FDOCT)

CLAIM OF PRIORITY

The present application claims priority from U.S. Provisional Application No. 60/881,201; filed Jan. 19, 2007, the disclosure of which is hereby incorporated herein by reference as if set forth in its entirety.

STATEMENT OF GOVERNMENT SUPPORT

This invention was made with government support under grant number 2R44EY015585 awarded by National Institutes of Health, National Eye Institute. The United States Government has certain rights in this invention.

FIELD OF THE INVENTION

The present invention relates to imaging systems and, more particularly, to optical coherence imaging systems.

BACKGROUND OF THE INVENTION

Optical coherence tomography (OCT) is a rapidly advancing imaging modality with broad applications in biomedical and industrial imaging. Originally reduced to practice at MIT in the early 1990's, the first generation of OCT achieved clinical success as a diagnostic tool for retinal pathologies. This first generation technology relied on a moving reference mirror in a fiber-interferometric geometry. The interferometer output a signal whose strength squared was in direct proportion to backscattered power of light from within the subject under test, specifically at the depth where the path length into the sample matched the path length to the movable reference mirror. This technique is known as a time-domain technique, and advantages in simplicity of architecture and signal interpretation are overcome by a low signal-to-noise ratio and slow imaging speed.

More recently, a new class of OCT imaging technology has emerged that may address some of the disadvantages of the time-domain approach. Fourier domain OCT relies on acquiring a frequency-domain signature and polling the depth of the sample in one pass. This parallel acquisition of the depth-dependent backscattered light leads to from about 15 to about 20 dB increase in the signal to noise ratio (SNR), and this advantage in SNR may readily be turned to faster imaging, higher quality images, or both. Commercial systems that deploy Fourier domain technology have recently reached the market and are aiming at replacing first generation systems with systems that acquire images up to 50 times faster.

While this speed increase on its own is valuable to the user, the Fourier domain approach offers both additional advantages and additional complexity that offer associated benefits and risks. Generating an image in the Fourier domain approach requires Fourier-transformation of frequency domain (wavelength or wavenumber) data. Opportunities for optimizing Fourrier domain OCT imaging systems lie in real-time signal processing, image optimization, and management and utilization of the high data-content images.

SUMMARY OF THE INVENTION

Some embodiments of the present invention provide methods, systems and computer program products for managing frequency domain optical coherence tomography (FDOCT) image resolution. A spectrum used to acquire an image of a subject is calibrated and default dispersion correction parameters are set. Default dispersion management parameters associated with a region of the image of the subject are also set. The image of the subject is acquires after setting the default dispersion correction parameters and the default dispersion management parameters. A quality of the acquired image is compared to a quality metric for the acquired image. The dispersion correction parameters are adjusted if the quality of the acquired image does not meet or exceed the quality metric for the acquired image. The acquired image is reprocesses based on the adjusted dispersion correction parameters. The steps of comparing, adjusting and reprocessing are repeated until the acquired image meets or exceeds the quality metric for the acquired image.

In further embodiments of the present invention, the default dispersion correction parameters may be set zero.

In still further embodiments of the present invention, the step of acquiring the image is performed before calibrating the spectrum.

In some embodiments of the present invention, a spectrometer used to acquire an image of a subject may be calibrated.

In further embodiments of the present invention, the adjusted dispersion correction parameters may be stored as the default dispersion correction parameters for a class of subjects. In certain embodiments, a second image of a same subject or another subject in the class may be processed using the stored adjusted dispersion correction parameters.

In still further embodiments of the present invention, the acquired image may be automatically optimized without any user intervention. The comparing, adjusting, reprocessing and repeating may be performed automatically to optimize the acquired image without any user intervention for a class of subjects.

In some embodiments of the present invention, the processing may be distributed among two or more central processing units (CPUs) to reduce processing time.

In further embodiments of the present invention, the acquired image may be displayed; a line or frame for optimization may be chosen; a region on the chosen line or frame may be selected to optimize; and the acquired image may be reprocessed based on the selected region on the chosen line or frame.

In still further embodiments of the present invention, the region of the image may include a three dimensional volume, a two dimensional frame or subset of a frame, a line or a subset of a line.

In some embodiments of the present invention, a portion of a target subject to be imaged may be selected in a control window using an overlay tool. The image may be acquired and reprocessed based on the selected portion of the acquired image. The selected portion of the acquired image may have a shape that is quadrilateral, annular, circular or linear. The image may be acquired and reprocessed in real time as the portion of the acquired image is selected in the control window.

Further embodiments of the present invention provide methods, systems and computer program products of processing data. An image is acquired and raw frequency domain data associated with the acquired image is stored in a temporary or permanent data archive. The stored frequency domain data is processed to provide improved images.

In further embodiments of the present invention, the image is obtained using a frequency domain optical coherence tomography (FDOCT) system and algorithms may be applied to the stored raw frequency domain data during at least one step of a processing pipeline to provide improved images acquired using FDOCT. Processing may further include applying fast fourier transform (FFT) algorithms to the stored raw frequency domain data; applying windowing functions to the FFT algorithms; applying filtering functions to the FFT algorithms; applying phase-dependent operations between time- or space-separated data elements; applying dispersion compensation algorithms to the stored raw frequency domain data; applying spectral calibration algorithms to the stored raw frequency domain data; and/or applying averaging algorithms to the stored raw frequency domain data. The averaging algorithms may be directly accessible by a user.

In still further embodiments of the present invention, the averaging algorithms may include line averaging including acquiring a plurality of depth lines in one lateral location for averaging, moving to a next lateral location, and averaging the plurality of depth lines for each location; moving window averaging including acquiring a lateral scan including a plurality of depth lines and averaging a user-specified contiguous subset of adjacent depth lines; and frame registration averaging including registration of m lateral scans of n depth lines to each other and averaging the m complete lateral scans of the n depth lines.

In some embodiments of the present invention, space domain data may be stored along with the raw frequency domain data.

In further embodiments of the present invention, a metadata file may be associated with the raw frequency domain data. The data may be processed on demand processing into space domain data.

In still further embodiments of the present invention, the image may be obtained using a frequency domain optical coherence tomography (FDOCT) system and the raw frequency domain data and metadata may be stored remote from imaging hardware of the FDOCT and/or the point of analysis. The raw frequency domain data may be processed into space domain data remotely.

In some embodiments of the present invention, the raw frequency domain data may include subject specific information and/or hardware specific information used to associate the raw frequency domain data to a subject and/or to a specific piece of imaging hardware.

In further embodiments of the present invention, user controlled processing of the raw frequency domain data may be used such that user-desired information is extracted or user-desired images are generated.

In still further embodiments of the present invention, steps of the process may be recorded as metadata such that generated data can be recreated from original raw frequency domain data, original metadata, and/or operationally defined metadata.

Some embodiments of the present invention provide methods, systems and computer program products for displaying images acquired using frequency domain optical coherence tomography (FDOCT) systems. A volume intensity projection (VIP) image is displayed by displaying a weighted sum of depth-dependent data over at least a subset of a lateral scan range. The weighting may be uniform over an entire depth, uniform over a selected depth, or non-uniform over the entire depth or a selected depth. In certain embodiments, the weighting function is controlled by the user through access to two or more control items that indicate a center position of summed data and the range of the summed data. The weighting function may be controlled by the user through access to two or more control items that indicate on a cross-sectional subset of the data the center position of the summed data and the range of the summed data. The range of the summed data may include boundaries of a uniform sum or a parametric representation of a non-uniform sum.

Further embodiments of the present invention provide methods, systems and computer program products for obtaining values of optimized dispersion parameters for a subject using a frequency domain optical coherence tomography (FDOCT) system. The optimized subject dispersion parameters may be obtained based on the following equations:

$$D1=dD+Ds;$$

$$D2=dD+Dr;$$

$$Ds=(D1-D2)+Dr,$$

where D1 equals the series dispersive terms obtained through image optimization of a subject, D2 equals the series dispersive terms obtained through image optimization of a reference sample, dD equals the algebraic difference between the dispersive terms obtained for the subject and the reference sample, Ds equals the ordered series dispersion terms of the subject and Dr equals the ordered series dispersion terms for the reference sample.

In still further embodiments of the present invention, the dispersive terms Dx may be an ordered set of dispersion terms representative of mathematical Taylor series expansion of phase terms. The optimized dispersion parameters of a reference sample may be obtained on a system used for obtaining values for the subject. The reference sample may have a known set of physical dispersion parameters. The reference sample may have a known dispersion, including higher order dispersion including one or more of group velocity (beta__1), group velocity dispersion (beta__2), and slope of group velocity dispersion (beta__3).

BRIEF DESCRIPTION OF THE DRAWINGS

FIG. 20 is a screen shot illustrating Hardware window, probe tab according to some embodiments of the present invention.

FIG. 21 is a block diagram illustrating the organization of processing steps as a multi-threaded pipeline and divided among the available processors according to some embodiments of the present invention.

DETAILED DESCRIPTION OF THE INVENTION

Figure 1:
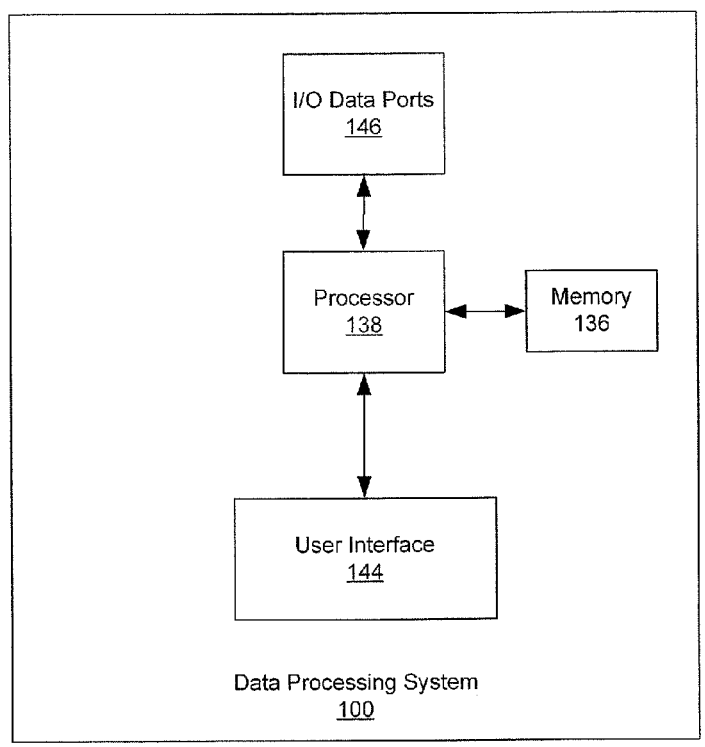
FIG. 1 is a block diagram of a data processing system according to some embodiments of the present invention.

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

It will be understood that, although the terms first, second, etc may be used herein to describe various elements, these elements should not be limited by these terms. These terms are only used to distinguish one element, from another element. Thus, a first element discussed below could be termed a second element without departing from the teachings of the present invention.

The present invention may be embodied as methods, systems and/or computer program products. Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The present invention is described below with reference to block diagrams and/or flowchart illustrations of methods, systems and computer program products according to some embodiments of the invention. It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

Methods, systems and computer program products for processing and reprocessing images generated using frequency domain optical coherence tomography (FDOCT) will now be discussed with respect to FIGS. 1 through 22. Referring first to FIG. 1, an exemplary embodiment of a data processing system 100 suitable for use in an FCODT system in accordance with some embodiments of the present invention will be discussed. The data processing system 100 typically includes a user interface 144, such as a keyboard, keypad, touchpad or the like, I/O data ports 146 and a memory 136 that communicate with a processor 138. The I/O data ports 146 can be used to transfer information between the data processing system 100 and another computer system or a network. These components may be conventional components, such as those used in many conventional data processing systems, which may be configured to operate as described herein.

Figure 2:
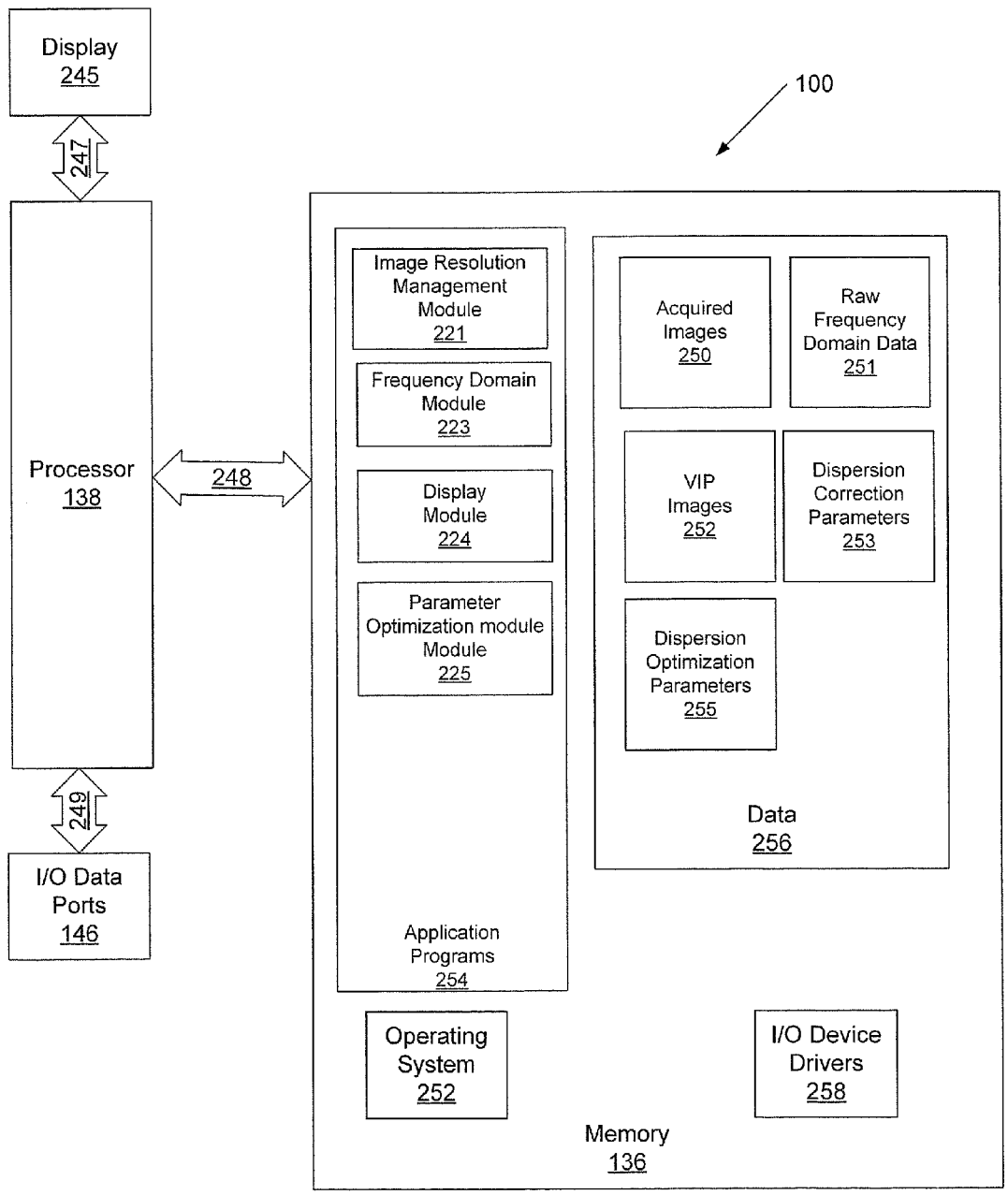
FIG. 2 is a more detailed block diagram of data processing systems according to some embodiments of the present invention.

Referring now to FIG. 2, a more detailed block diagram of the data processing system 100 in accordance with some embodiments of the present invention will be discussed. The processor 138 communicates with a display 245 via and address/data bus 247, the memory 136 via an address/data bus 248 and the I/O data ports 146 via an address/date bus 249. The processor 138 can be any commercially available or custom microprocessor. The memory 136 is representative of the overall hierarchy of memory devices containing the software and data used to implement the functionality of the data processing system 100. The memory 136 can include, but is not limited to, the following types of devices: cache, ROM, PROM, EPROM, EEPROM, flash memory, SRAM, and DRAM.

As shown in FIG. 2, the memory 136 may include several categories of software and data used in the data processing system 100: an operating system 252; application programs 254; input/output (I/O) device drivers 258; and data 256. As will be appreciated by those of skill in the art, the operating system 252 may be any operating system suitable for use with a data processing system, such as OS/2, AIX or zOS from International Business Machines Corporation, Armonk, N.Y., Windows95, Windows98, Windows2000 or WindowsXP from Microsoft Corporation, Redmond, Wash., Unix or Linux. The I/O device drivers 258 typically include software routines accessed through the operating system 252 by the application programs 254 to communicate with devices such as the I/O data port(s) 146 and certain memory 136 components. The application programs 254 are illustrative of the programs that implement the various features of the data processing system 100 included in an FDOCT system and preferably include at least one application that supports operations according to some embodiments of the present invention. Finally, the data 256 represents the static and dynamic data used by the application programs 254, the operating system 252, the I/O device drivers 258, and other software programs that may reside in the memory 136.

As illustrated in FIG. 2, the data 256 according to some embodiments of the present invention may include images acquired from a subject 250, raw frequency domain data 251, volume intensity projection (VIP) images 252, dispersion correction parameters 253 and dispersion management parameters 255. Although the data 256 only includes five different types of 250, 251, 252, 253 and 255, embodiments of the present invention are not limited to this configuration. There may be two or more of any of the types of data included in the data 256 or different types of data without departing from the scope of the present invention.

As further illustrated in FIG. 2, the application programs 254 may include an image resolution management module 221, a frequency domain module 223, a display module 224 and a parameter optimization module 225 according to some embodiments of the present invention. While the present invention is illustrated, for example, with reference to the image resolution management module 221, the frequency domain module 223, the display module 224 and the parameter optimization module 225 being application programs in FIG. 2, as will be appreciated by those of skill in the art, other configurations may also be utilized while still benefiting from the teachings of the present invention. For example, the image resolution management module 221, the frequency domain module 223, the display module 224 and the parameter optimization module 225 may also be incorporated into the operating system 252 or other such logical division of the data processing system 100. Thus, the present invention should not be construed as limited to the configuration of FIG. 2, but is intended to encompass any configuration capable of carrying out the operations described herein.

Furthermore, while the image resolution management module 221, the frequency domain module 223, the display module 224 and the parameter optimization module 225 are illustrated in a single data processing system, as will be appreciated by those of skill in the art, such functionality may be distributed across one or more data processing systems. Thus, the present invention should not be construed as limited to the configuration illustrated in FIGS. 1 through 2, but may be provided by other arrangements and/or divisions of function between data processing systems.

In particular, the image resolution module 221 is configured to optimize FDOCT image resolution. It will be understood that methods, systems and computer program products according to some embodiments of the present invention, may optimize memory usage for reprocessing or for display on the display 245. Optimizing for reprocessing may consume a greater amount of memory. Optimizing for display may limit or even prevent reprocessing, but also may allow the capture and display of many more lines of data. The specific functionalities of the image resolution module 221 will be discussed further below with respect to the block diagram of FIG. 3 and the flowcharts of FIGS. 5 through 7.

The frequency domain module 223 is configured to store raw frequency domain data and process/reprocess the raw frequency domain data at various stages of image processing. Details of the frequency domain module 223 will be discussed further below. The display module 224 is configured to display images acquired using frequency domain optical coherence tomography (FDOCT) systems. In particular, the display module may be configured to display a VIP image by displaying a weighted sum of depth-dependent data over at least a subset of a lateral scan range as will be discussed further below. Finally, the parameter optimization module 225 is configured to obtain values of optimized parameters for an FDOCT system as will be discussed further below.

Although embodiments of the present invention are discussed herein with respect to many processing and display embodiments, embodiments of the present invention are not limited to these specific embodiments. For example, in some embodiments of the present invention certain advanced measurements may be enabled by the features of the present invention. In particular, in some embodiments of the present invention, the group velocity dispersion (beta__2) and slope of the group velocity dispersion (beta__3) may be measured for a sample under test.

Operations of the image resolution management module 221 will now be discussed with respect to the flowcharts of FIGS. 5 through 7. Referring first to the flowchart of FIG. 5, operations for optimizing FDOCT image resolution in a spectral domain implementation begin at block 500 by calibrating a spectrum used to acquire an image of the subject. In some embodiment of the present invention, for example, spectral domain or "spectral radar" implementations, a spectrometer may be used to acquire an image of a subject and may be calibrated. In further embodiments of the present invention, for example, swept source implementations, the frequency-dependent spectrum as acquired in a temporally serial fashion is used to acquire an image of a subject and this may be calibrated. Accordingly, calibrating the spectrum according to some embodiments of the present invention encompasses any type of spectral calibration known to those having skill in the art. As used to acquire an image of a subject. As used herein, "subject" refers to any subject that can be effectively imaged using and FDOCT system in accordance with some embodiments of the present invention. In some embodiments, the subject may be a human eye.

Operations continue at blocks 510 and 520 by setting default dispersion correction parameters and setting default dispersion management parameters associated with a region of the image of the subject, respectively. It will be understood that in some embodiments of the present invention, the dispersion correction default may be zero without departing from the scope of the present invention. Furthermore, "setting default management parameters" refers to setting a region to be optimized and the region may be any subset of pixels. The region of the image may be, for example, a three dimensional volume, a two-dimensional frame or subset of a frame, a line or a subset of a line without departing from the scope of the present invention. Dispersion optimization and parameters associated therewith are discussed in detail in commonly assigned United States Patent Publication No. US-2007-0258094, filed Apr. 24, 2007 to Brown et al., entitled Methods, Systems and Computer Program Products for Optical Coherence Tomography (OCT) Using Automatic Dispersion Compensation, the disclosure of which is hereby incorporated herein by reference as if set forth in its entirety.

In some embodiments of the present invention, the image resolution management module 221 is configured to provide multiple resolution-optimizing algorithms to provide a user of the FDOCT system flexibility to choose to optimize on the basis of, for example, processing speed, resolution uniformity versus depth and/or best resolution at a depth.

Image sharpness is a function of accurate dispersion compensation between reference and sample paths. Dispersion compensation to first order is accomplished by hardware path matching. This is generally suitable only to a certain extent, as precise component matching is difficult in practice, and as each sample to be imaged will, in general, have different dispersive characteristics, i.e., each subject is unique.

Methods, systems and computer program products according to some embodiments of the present invention may provide algorithms that can be applied to optimize dispersion though an expansion of phase terms in the transform equations that define the relationship between the Fourier and spatial domains. Two methodologies for applying such phase terms have been defined, and are termed the "spectral scaling" and "Hilbert transform" approaches. Other approaches are also possible, for example, as discussed in Unites States Patent Publication No. 2007-0258094, incorporated herein by reference above.

These phase parameters are directly related to higher-order dispersion. As will be discussed further below, in some embodiments of the present invention, the software is configured to search for the parameters that optimize a metric of image quality. The applied metric may be used to increase or possibly maximize pixel brightness across the image. Other metrics may also possible without departing from the scope of the present invention. In some embodiments, the exact value of the dispersion parameters is not the important result; rather it is the quality of the obtained image.

In further embodiments of the present invention, the value of the optimized parameters may be of primary interest. Specifically, because dispersive properties of materials are, in general, linear optical properties, the dispersion of one sample may be determined through reference to a second subject of known dispersion.

For example, if we let D1 equal the dispersive terms obtained through image optimization of a sample and D2 equal the dispersive terms obtained through image optimization of a reference, then if we further allow that dD equals the differential dispersion between subject-free reference and sample paths and Ds equals the ordered dispersion of the sample and Dr equals the ordered dispersion of the reference, then we note that:

$D1=dD+Ds$ $D2=dD+Dr$ $Ds=(D1-D2)+Dr.$

These operations may be performed by the parameter optimization module 225 of FIG. 2.

In some embodiments of the present invention, the dispersive terms Dx may be an ordered set of dispersion terms representative of mathematical Taylor series expansion of phase terms. In some embodiments of the present invention, the optimized dispersion parameters of a reference sample may be obtained on a system used for obtaining values for the subject. In some embodiments of the present invention, the reference sample has a known set of physical dispersion parameters, including higher order dispersion including one or more of group velocity (beta__1), group velocity dispersion (beta__2), and slope of group velocity dispersion (beta__3).

Referring again to FIG. 5, operations continue at block 530 by acquiring the image of the subject. The image is acquired sometime after the default dispersion correction parameters have been set. The image may be acquired before or after the spectrum is calibrated without departing from the scope of the present invention. A quality of the acquired image may be compared to a quality metric for the acquired image (block 550). It is determined if the quality metric for the acquired image is met by the acquired image (block 560). If it is determined that the quality metric has not been met (block 560), the dispersion correction parameters may be adjusted (block 570) and the acquired image may be reprocessed based on the adjusted dispersion correction parameters (block 580). In some embodiments of the present invention, the acquired image may be reprocessed in the space domain (equivalently, time domain). Operations of blocks 550 through 580 may be repeated until the acquired image meets or exceeds the quality metric for the acquired image.

If, on the other hand, it is determined that the acquired image meets the quality metric for the acquired image (block 560), operations for optimizing FDOCT image resolution may cease. As will be discussed further below with respect to block 690 of FIG. 690. The dispersion parameters used to obtain the image that meets the quality metric may be stored and used for further image of this or another subject. The subject may be a member of a class of subjects, and the dispersion parameters of the subject may be used for further imaging of other subjects within the class. It will be understood that optimal dispersion parameters obtained for one subject or class may not be a better starting point for a second subject or class than the default parameters of the FDOCT system.

Figure 5:
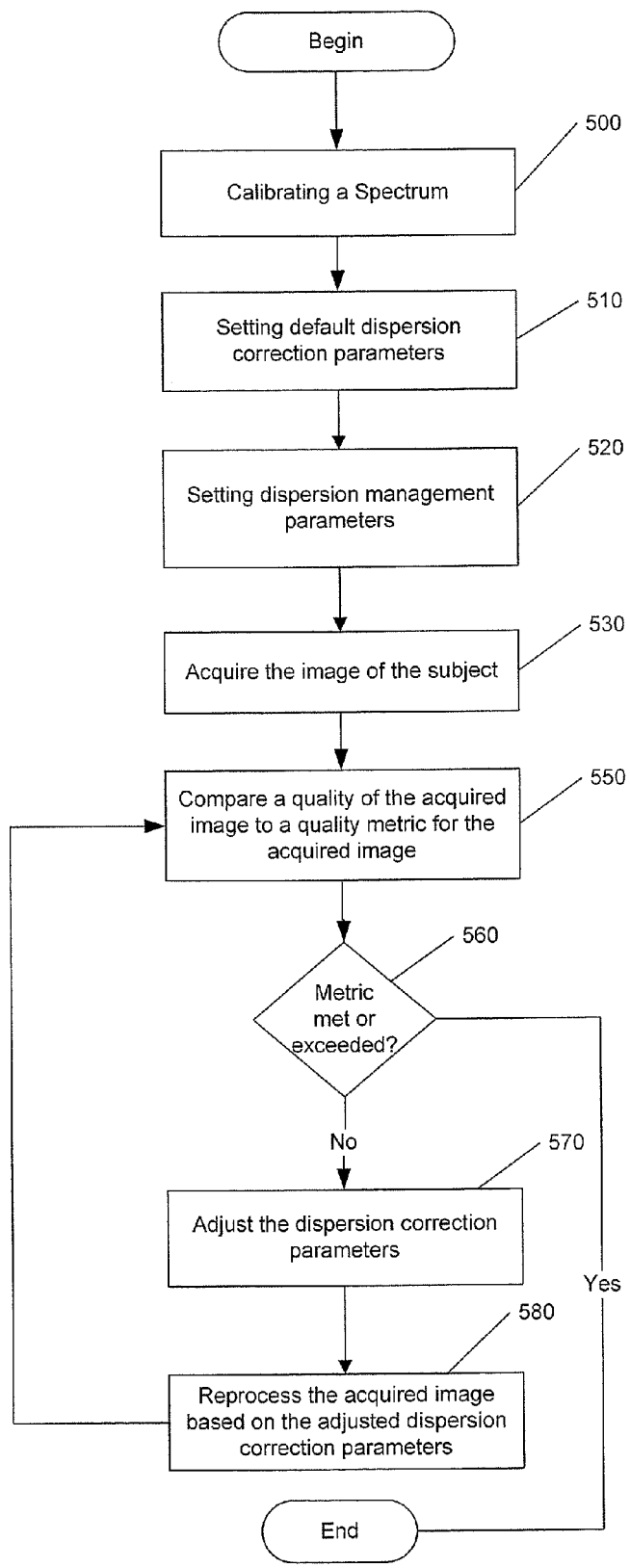
FIGS. 5 through 8 are flowcharts illustrating operations according to various embodiments of the present invention.

In embodiments of the present invention that use auto-optimization features according to some embodiments of the present invention, operations of blocks 550 through 580 of FIG. 5 may be performed without any intervention from the user of the FDOCT system.

Figure 6:
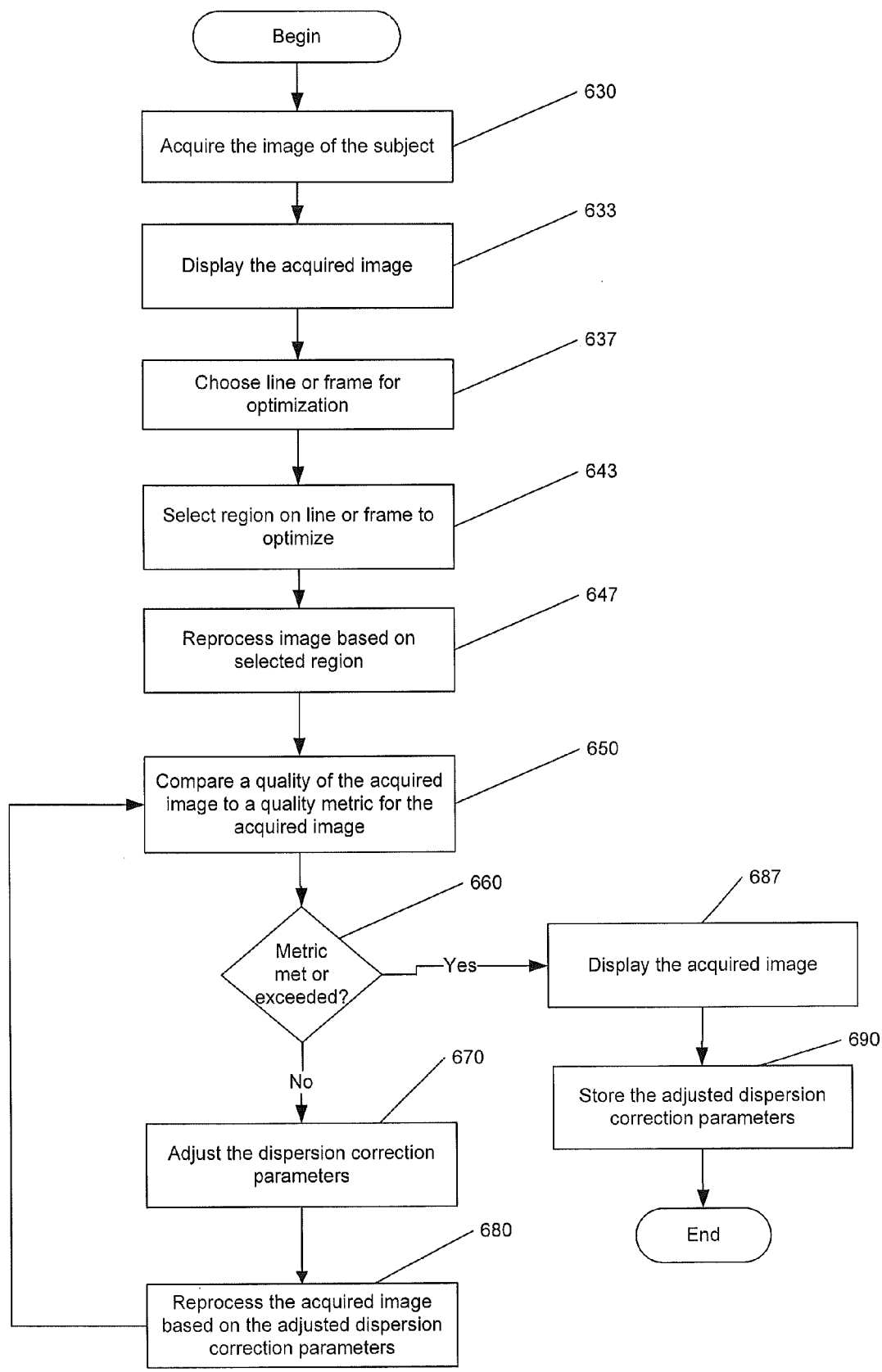

Referring now to the flowchart of FIG. 6, operations for optimizing FDOCT image resolution begin as discussed above with respect to blocks 500 and 510 and 520 of FIG. 5. Operations continue at block 630 by acquiring an image of the subject. In embodiments of the present invention discussed with respect to FIG. 6, the acquired image may be displayed, for example, on display 245 of FIG. 2. A line or frame or other region for optimization may be chosen (block 637). A region on the chosen line or frame to optimize may be selected (block 643).

Figure 3:
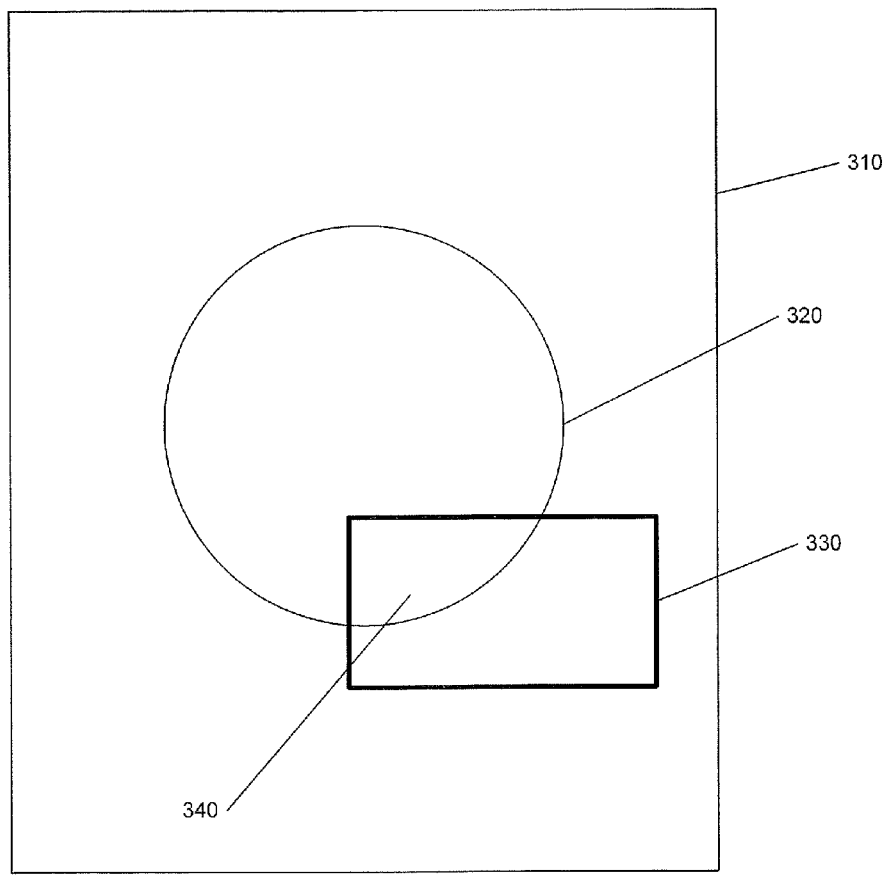
FIG. 3 is a control window and an overlay tool according to some embodiments of the present invention.

In some embodiments of the present invention, the selection associated with block 643 may be made by selecting a portion of the image to be acquired 340 in a control window 310 using an overlay tool 330 as illustrated in FIG. 3. In particular, referring to the block diagram of FIG. 3, the control window 300 provides a picture of the subject 320. The overlay tool 330 can be used to highlight the portion 340 of the subject 320 that is of interest and that will be scanned. Although the overlay tool 330 is illustrated as rectangular in FIG. 3, embodiments of the present invention are not limited to this configuration. For example, the overlay tool 330 may be, for example, square, circular, linear or the like without departing from the scope of the present invention. The overlay tool 330 may be used to extend, rotate, move, change or the like where on the subject 320 the scan will occur. The image may be reprocessed based on the portion 340 of the acquired image selected using the overlay tool 330. The overlay tool 330 may be registered with the sample. Thus, according to some embodiments of the present invention the image may be reprocessed in real time (Live) as the portion of the acquired image 340 is selected in the control window 310 using the overlay tool 330.

In some embodiments of the present invention, simple user accessible tools, such as the overlay tool 330, are provided to set up and control the multi-dimensional imaging functionality. As discussed above, a window may be provided in which the central position, lengths in up to two lateral dimensions, and angle of the scan may be set within the time frame of one B-scan using a simple graphical tool that may be mouse or joystick controlled.

In some embodiments of the present invention, within this dynamic control window (scan window 310) is a 2-dimensional image 320 representing the object to be imaged. This image may have originated directly from a recently acquired OCT scan or any other method to acquire a representation of the object to be scanned, including video or CCD photography.

In some embodiments of the present invention, this reference image in the dynamic control window is calibrated and scaled to the OCT imaging control in order to effect precise control of the scanning beam. Graphical elements may be used to manipulate the scan control, these graphical elements may be overlaid on the representative image, and the graphical elements may be selected from a selection of graphical elements, such as lines, squares, circles, rectangles and ellipses or other such graphical elements as may represent the structure of a desired scan pattern.

In some embodiments of the present invention, a series of selectable scan patterns may be provided that are at the immediate user control. Scan patterns may be drawn from the family of M-mode scans, Linear B-scans, rectangular volume scans, radial scans, and annular scans.

In some embodiments of the present invention, scan patterns are established by setting a defined set of parameters appropriate to each scan type, including scan length, scan width, scan angle, scan offset in zero, one, or two directions, the number of lines per scan frame, the number scan frames per volume, and the number of volumes per image acquisition cycle.

In some embodiments of the present invention, a multiplicity of scan patterns, and specifically one scan pattern per scan type can be set by the user and persist until actively changed by the user to facilitate obtaining a series of scan types and repeating the scanning without resetting the scan patterns.

In some embodiments of the present invention, the parameters from one scan type that may be logically applied to another scan type may be, at the users discretion, transferred through "one click" to the second scan type.

Thus, some embodiments of the present invention incorporate a dynamic scan feature wherein the scan pattern may be altered on the fly. Under normal steady state scanning conditions, some embodiments of the present invention direct the scanning hardware to continuously output a scan pattern synchronized with data capture.

When a dynamic change is desired during scanning, some embodiments of the present invention capture the change, calculate the new scan pattern, and update the hardware. This update may be done during the inactive, retrace period of the scan.

In some embodiments of the present invention, the update may done by calculating the number of lines required for the update at the present scan line frequency, waiting until the proper location of the scan is reached, and updating the scan prior to the start of a new scan line.

Referring again the flowchart of FIG. 6, the acquired image may be reprocessed based on the selected region on the chosen line or frame (block 647). A quality of the reprocessed acquired image may be compared to a quality metric for the acquired image (block 650). It is determined if the quality metric for the acquired image is met by the acquired image (block 660). If it is determined that the quality metric has not been met (block 660), the dispersion correction parameters may be adjusted (block 670) and the acquired image may be reprocessed based on the adjusted dispersion correction parameters (block 680). Operations of blocks 650 through 680 may be repeated until the acquired image meets or exceeds the quality metric for the acquired image.

If, on the other hand, it is determined that the acquired image meets the quality metric for the acquired image (block 660), the acquired image meeting the quality metric may be displayed (block 687) on a display, for example, display 245 of FIG. 2. The adjusted dispersion correction parameters used to acquire the image that met the quality metric may be stored as the default dispersion correction parameters (block 690).

Figure 7:
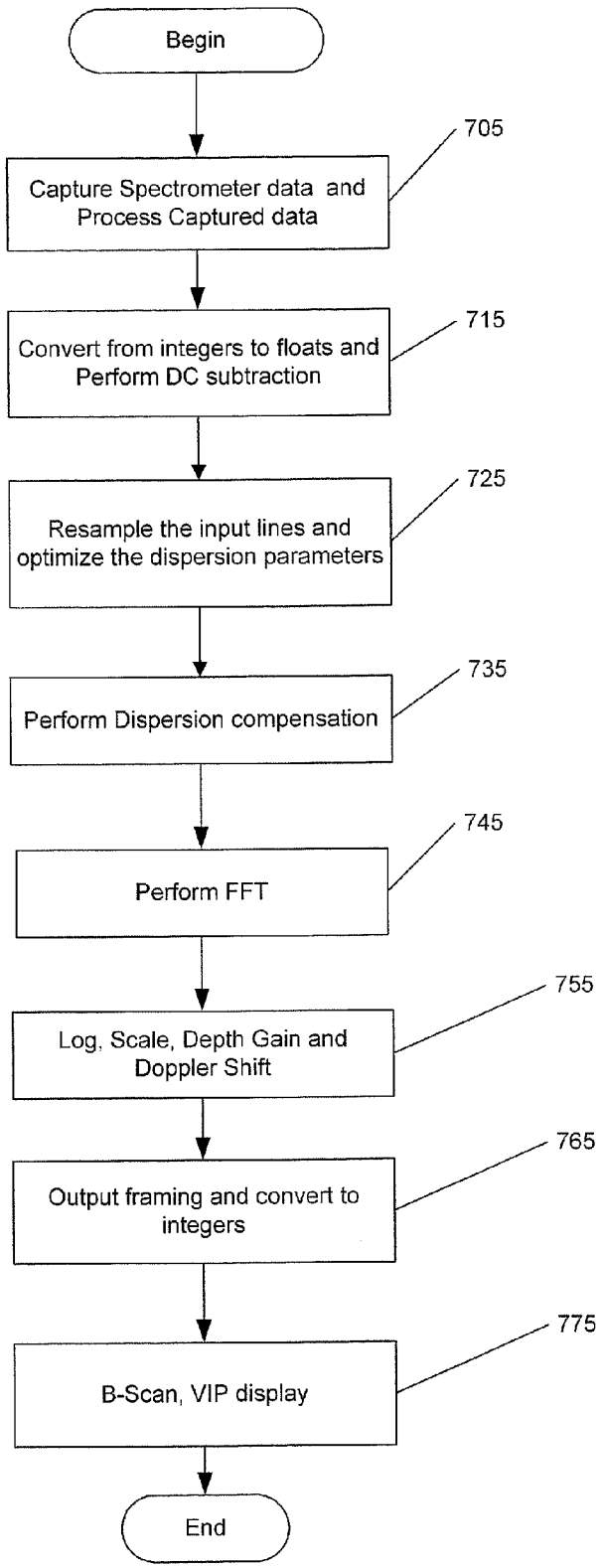

Referring now to FIG. 7, operations of processing pipelines according to some embodiments of the present invention will be discussed. As illustrated in FIG. 7, operations begin at block 705 by pre-processing. Preprocessing includes capturing spectrometer data and processing the captures data into frames. In particular, the spectrometer data is captured using a cameralink interface. For example, 12 bit data can be captured in 16 bit words in 2048 pixel lines at 17 khz, or about a 35 Mhz sample rate. The captured data may be processed into image frames. For example, 1024 of the 2048 input samples may be extracted and composed into images of 500 lines—10,000 lines and 20-200 inactive lines captured during galvanometer retrace may be stripped out. In some embodiments, the images may be 1000 lines.

Operations continue at block 715 by converting incoming lines and performing per-line dc subtraction. In particular, incoming lines may be converted from 16 bit integers into 32 bit floats. Per-line dc subtraction may be performed. Each sample location may be averaged over an entire frame and this value may be subtracted from the next frame.

The sample may be resampled and the dispersion parameters may be optimized (block 725). In particular, the 1024 sample input lines may be resampled into 2048 sample output lines. In pseudocode: for each i,j=lookup[i]; Out[i]=in[j]*weightA[i]+in[j+1]*weightB[i]. Dispersion parameter optimization as discussed above may be performed.

Dispersion compensation may be performed (block 735). In particular, dispersion compensation may be performed on each of the 2048 sample lines, producing a 2048 sample complex result. This may involve converting each line to complex floating point and setting the phase angle for each sample to a fixed value. The phase value is different for each sample and is computed on-demand above by the optimization routine.

A fast Fourier transform (FFT) may be performed on each of the 2048 sample complex float input lines, producing a 1024 sample complex floating point output line (block 745). Operations continue at block 755, by converting the 1024 sample complex floating point input lines into a 1024 sample real float by computing the magnitude of each sample; taking the log of each sample, multiplying the input line with a gain vector; multiplying the input by a scalar; resampling the input line into one of equal or shorter length, for example, resampling each 1024 sample input line to a 788 sample output line; taking the phase of the original input to the stage and accumulate it over the number of Doppler lines if Doppler is being calculated; and averaging the b-scan data from all previous steps of block 755 if Doppler is being calculated.

The image and Doppler float inputs may be converted to 16 bit integer data and the output lines may be assembled into image frames (block 765). The result may be displayed, for example, the B-Scan or VIP (block 775). Specific embodiments discussed above with respect to FIG. 7 are provided for exemplary purposes only and, therefore, embodiments of the present invention are not limited by these examples.

Operations of the frequency domain module 223 will now be discussed. Fourier Domain Optical Coherence Tomography (FDOCT) imaging systems provide a unique challenge in data management relative to previous generation time-domain optical coherence tomography systems (TDOCT). There are two significant differences in the data pipeline between FDOCT and TDOCT systems. First, as the terminology suggests, there is a mathematical transform relationship between the detected signals of TDOCT and FDOCT. In TDOCT, the detected optical signal is a time varying signal directly proportional to backscattering as a function of depth in a target sample. In FDOCT, the detected signal is acquired as a function of optical frequency, and the depth dependent scattering signature equivalent to the TDOCT signal is derived only after a Fourier transformation of the information from frequency to time (where time is related to depth through knowledge of the velocity of light). Second, because FDOCT enables data acquisition up to two orders of magnitude faster than TDOCT, the sheer volume of data that may be acquired scales commensurately.

Typically, the frequency-domain information itself is not of diagnostic interest, and the transformed time-domain data is the information to be presented and stored. As discussed further herein, this data management methodology may be wasteful of information uniquely available in the frequency-domain. Thus, according to some embodiments of the present invention, the raw frequency domain data may be stored in a data archive in addition to or instead of storing the space domain data.

Storing the data as acquired in the frequency domain may provide data that is truly archival. For example, storing the data as acquired in the frequency domain may be nominally equivalent to a trend in digital photography of storing data as acquired off of the digital sensor plane. In digital photography, this data is referred to as RAW data, or as a Digital Negative (.dng, Adobe Systems). Storing data as a Digital Negative may allow for customized software "development," where essential corrections to exposure, contrast, and color, for example, can be made outside of the camera. This may provide a degree of flexibility and subsequent image quality that can not be replicated when data is stored in a "developed" form, such as JPEG. Furthermore, the development is represented by an algorithm stored as metadata with the Digital Negative. Multiple developments may be efficiently stored, not by duplicating the image, but by storing multiple versions of the development metadata (cf Adobe Lightroom). This provides a very space efficient process for maintaining an archival data set with user-defined images.

This concept is extensible to transform data sets, and specifically to the transform data sets that define FDOCT images as discussed according to some embodiments of the present invention. Furthermore, there may be advantages to preserving the ability to develop images off the original raw Fourier data (Fourier Digital Negative). For example, these advantages may arise from specific information embedded in the frequency-domain data that typically cannot be readily recovered once the data is transformed. For example, spectral intensity and phase information present in the raw Fourier data can be utilized to modify images, extract additional information, or increase the effective imaging depth.

OCT generates high-resolution depth resolved images using the coherence gating behavior of broadband light interferometry. There is a direct inverse relationship between bandwidth and resolution. In this sense, OCT is a colorless technique. Chromatic effects in backscattering can be derived at the expense of resolution by filtering the spectrum before Fourier transformation. This may be particularly useful in the analysis of specific chromophores in the sample with signatures within the source bandwidth. These chromophores may be intrinsic to the sample, or may be specific contrast agents. Filtering to analyze specific spectral regions may reduce depth resolution, but when combined with the high resolution non-filtered spectrum, may provide a unique intersection between resolution and color. Conversely, this spectral filtering can be used to improve the effective resolution, at some cost to signal-to-noise ratio, by transforming a non-Gaussian spectral profile to a Gaussian profile, reducing the effect of ringing in the Fourier transform of the spectral shape. This filtering operation is done on the frequency domain data, but can be done post-acquisition, and does not typically require a physical optical filter in the system.

In general, a single spectral interferogram includes only intensity information. Motion within the sample, or generated within the instrument can be used to generate phase information. FDOCT with phase information may provide a broad toolset for further analysis. Motion, for example, flow, within the sample generates phase information in backscattering that can be applied to the Doppler measurements of sample velocity. Doppler measurements are generally derived from sequential lines scans acquired at one (x,y) position within the sample. Each line has a phase shift relative to the next owing to flow in the sample.

By way of further example, two additional uses for the phase variation associated with sample motion are in reduction of phase noise and in measurements of bulk sample motion. OCT is an interferometric technique, and interferometric speckle is the major cause of noise that cannot be resolved through increased detector integration. However, speckle originates in phase variations smaller than the wavelength of light; motion on this order can be used to average out speckle. Such fine motion can be less than one order of magnitude relative to the target resolution, and therefore speckle can be reduced or eliminated by inducing motion of this magnitude, or by taking advantage of micro-motion that always exists within living biological samples. This averaging is best performed in the frequency domain between data with phase variations on the order of speckle. Multiple modes of frequency domain averaging are possible, constrained only by the acquisition protocol used, and relative phase variation between data to be averaged. Examples of averaging modes include A-scan averaging and B-scan averaging. A-scan averaging can be accomplished on a series of static acquisitions, for example, $(x_1,y_1)=(x_2,y_2)$, in which case the phase variation originates in sample motion between integration periods. This method is equivalent to averaging the signals acquired for Doppler processing, which can be referred to as "Doppler averaging." This averaging mode may have limited effect in speckle reduction on a stable sample, but may also have a low risk of introducing undesirable artifacts. Alternatively, a moving window average can be implemented, where $(x_2,y_2)=(x_1+e,y_2+d)$, in which the phase variation includes a component originating in differences between different sample positions. This averaging mode can be quite effective in reducing speckle, but at the expense of introducing blurring artifacts. A third approach is time-separated averaging. In this case, a series of A-scans that form a 2-dimensional image, or B-scan, are acquired and averaged with the next sequential B-scan. For example, averaged line pairs (x1,y1), (x2,y2) are related by (x2,y2)=(x1+e+t,y1+d+t), where t is long enough such that fluctuations in system phase are sufficient to reduce speckle on averaging, and (e, d) are intentionally or unintentionally imposed, but small enough to minimize undesirable blurring.

In some embodiments of the present invention, alternatively to averaging out this phase noise, measurements of the phase changes have utility beyond Doppler flow measurements. In many cases, the subject under test has intrinsic bulk motion that is desirable to measure. One example is in regard to pulsation of the eyeball with the circulatory cycle. In 3D imaging the anterior of the eye, it is necessary to correct for the pulsatory motion. A direct method may take advantage of the cyclical phase variations to provide a correction formula for this motion.

It is well known that the addition of quadrature phase information to FDOCT signals enables the elimination of complex-conjugate artifacts and mirror images endemic to Fourier transformation of real (phase-free) signals. This complex-conjugate artifact reduction process typically requires specific phase information, and the operation occurs in the frequency domain.

One critical operation in the frequency domain is linearizing the acquired signal to wavenumber, or frequency, as the Fourier transformation process relies on a sequence of data evenly-spaced in frequency. In general, detection is approximately linear in wavelength, and a resampling into frequency is required. A higher order issue is the nonlinearity in wavelength of the spectral acquisition, due to the grating equation and any inaccuracies in the pixel placement of the detecting camera. Accurate calibration of the spectrometer for these effects is required for subsequent operations, including importantly software dispersion compensation as discussed in—9526-11. Similar calibrations are required in swept source implementations. Other operations in the frequency domain may include operations relative to polarization effects, and still other operations may be envisioned. It is nonetheless clear that significant interaction with the frequency domain data is desirable to increase the information extraction, and that archiving of the frequency domain data can preserve the dataset fundamental to frequency domain imaging and FDOCT.

In view of the above, some embodiments of the present invention store raw Fourier-domain data associated with an image acquired using FDOCT in a data archive. In other words, the raw Fourier-domain data is stored instead of or along with the space domain data. Thus, according to some embodiments, this raw Fourier-domain data may be processed to provide improved images acquired using FDOCT systems. Processing of the raw Fourier-domain data may include applying alternative or new algorithms relevant to any portion of the Fourier processing pipeline, i.e., the raw Fourier data can be processed at any point in the processing pipeline.

For example, new fast Fourier transforms (FFTs) algorithms, for example, FFT algorithms optimized for speed or to reduce aliasing, may be applied to the raw Fourier-domain data. In some embodiments of the present invention, windowing and filtering functions may be applied to FFT algorithms. The windowing and filtering functions may reduce or eliminate artifacts in the time domain data, improve computing speed and may allow selection of a subset of data that includes/excludes spectral features of interest. Thus, windowing may provide the ability to focus on particular features in an area of interest. In certain embodiments, windowing functions may be applied to two or more (multiple) spectral features and then, the results may be compared or a ration of the two may be determined. In some embodiments of the present invention, dispersion compensation algorithms may be applied to the raw Fourier-domain data. Dispersion compensation algorithms are discussed in detail in commonly assigned United States Patent Publication No. US-2007-0258094, filed Apr. 24, 2007 to Brown et al., entitled Methods, Systems and Computer Program Products for Optical Coherence Tomography (OCT) Using Automatic Dispersion Compensation, which has been incorporated by reference herein above. In some embodiments of the present invention, spectral calibration algorithms and/or averaging algorithms may also be applied to the raw Fourier-domain data.

In some embodiments of the present invention, frequency or space domain averaging functions may be embedded in the software application and directly accessible by the user.

In some embodiments of the present invention, three averaging modes may be addressable by the user: Line averaging, whereby the scanning system acquires a multiplicity of depth lines in one lateral location for averaging and then moves to the next lateral location, and the multiplicity of depth lines per location are averaged; Moving window averaging, whereby the scanning system acquires a typical lateral scan including a multiplicity of depth lines and the averaging entails averaging a user-specified contiguous subset of neighboring depth lines; and Frame registration averaging, whereby in complete lateral scans of n depth lines are registered to each other and averaged.

In some embodiments of the present invention, the user can turn the averaging feature on or off before or after a scan is acquired, subject to the appropriate lines and frames having been acquired.

In some embodiments of the present invention, the spectrum may be piecewise analyzed beginning with the stored raw frequency domain data for determining wavelength-dependent effects and the depth resolution is traded-off for spectral resolution.

In some embodiments of the present invention, the archived raw frequency domain data may be reprocessed using "one-click" functionality to evaluate the impact of any of the aforementioned features and measurements, or the impact of any new or alternative algorithms, or to be analyzed by as yet unconsidered techniques at any time following the initial measurement with no loss of information from the as-acquired state.

It will be understood that the examples of algorithms and functions discussed above are provided for exemplary purposes only and, therefore, embodiments of the present invention are not limited by these examples. Any functions or algorithms known to those of skill in the art may be applied to the stored raw Fourier-domain data without departing from the scope of the present invention.

It will be further understood that storing the raw Fourier-domain data may allow users to optimize the acquired image for their own FDOCT systems. For example, many optimization algorithms and functions exist. Some embodiments of the present invention allow for software plug-ins including new algorithms to be inserted in the processing pipeline.

Figure 8:
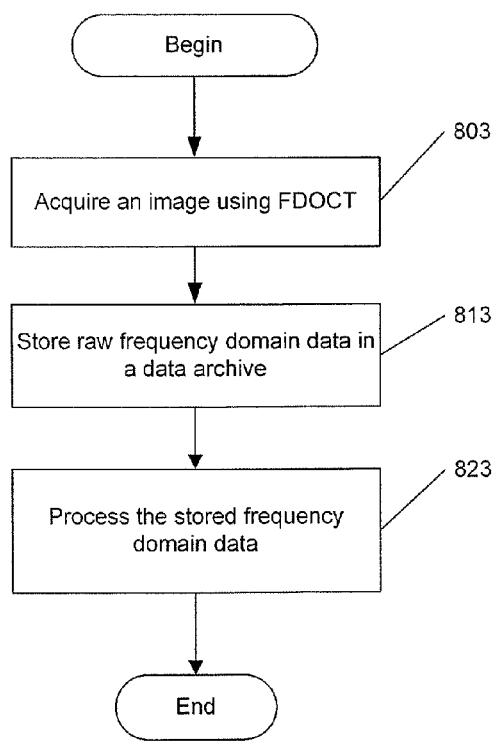
Figure 9:
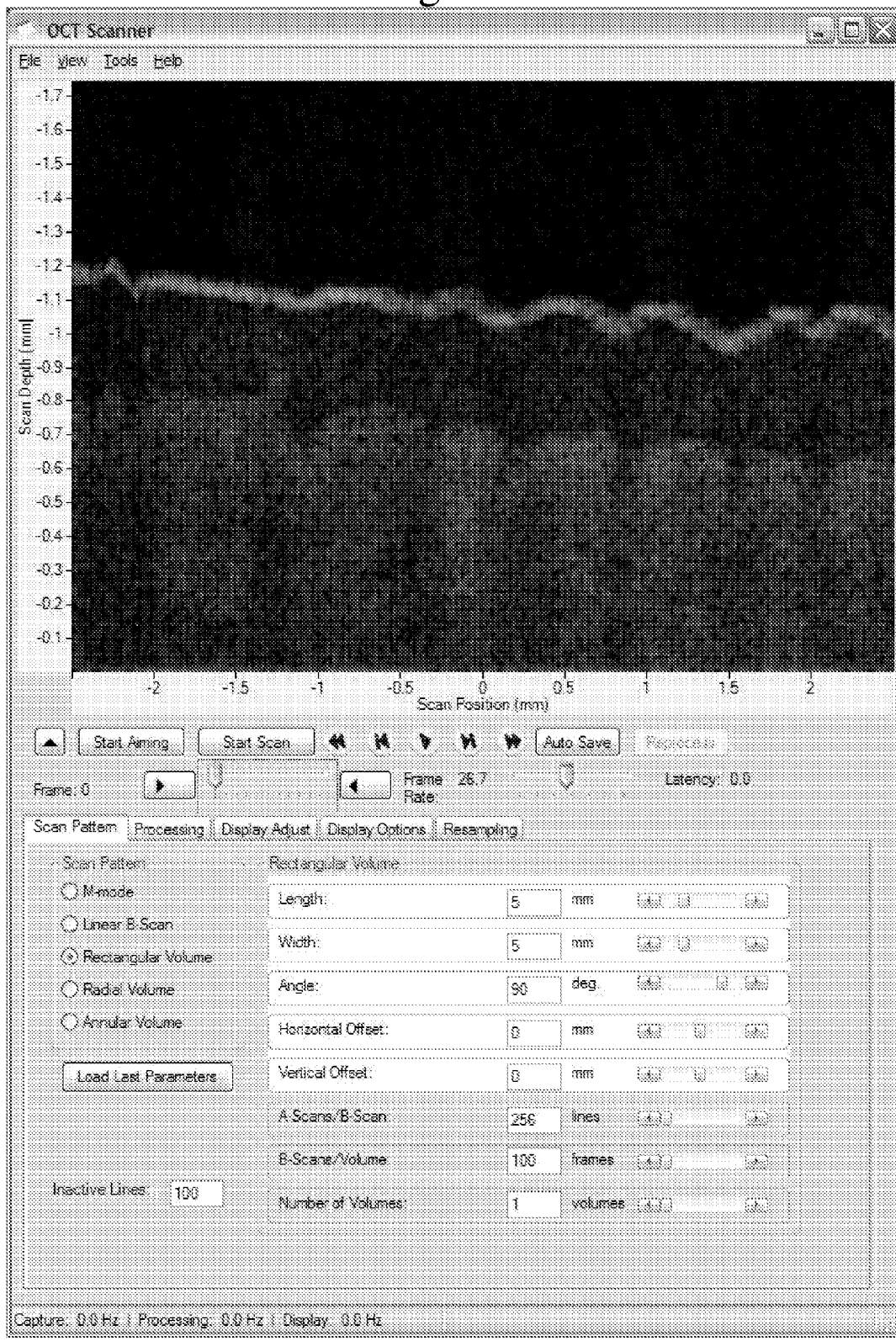
FIG. 9 is a screen shot illustrating the main window, scan tab according to some embodiments of the present invention.
Figure 10:
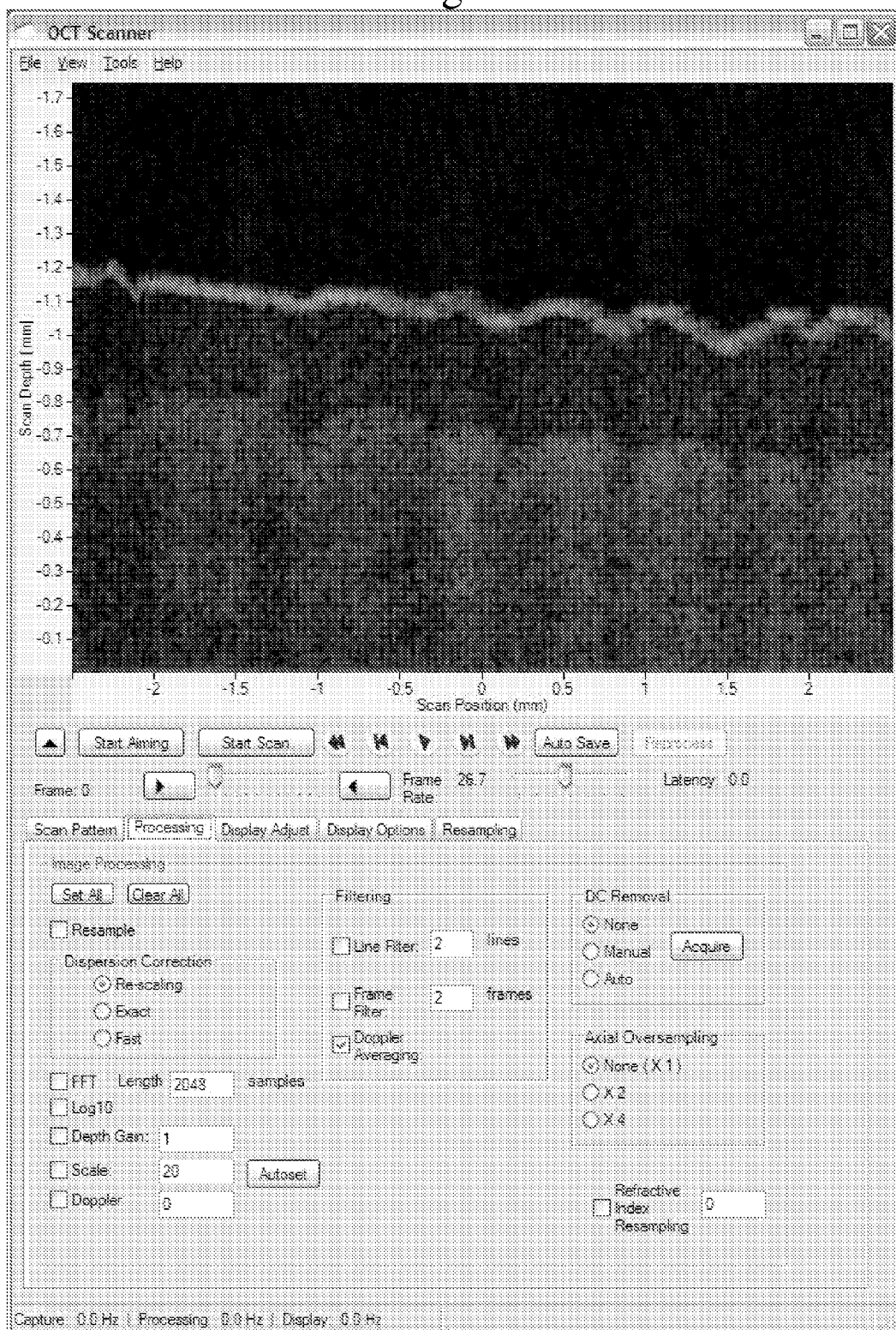
FIG. 10 is a screen shot illustrating the main window, processing tab according to some embodiments of the present invention.
Figure 11:
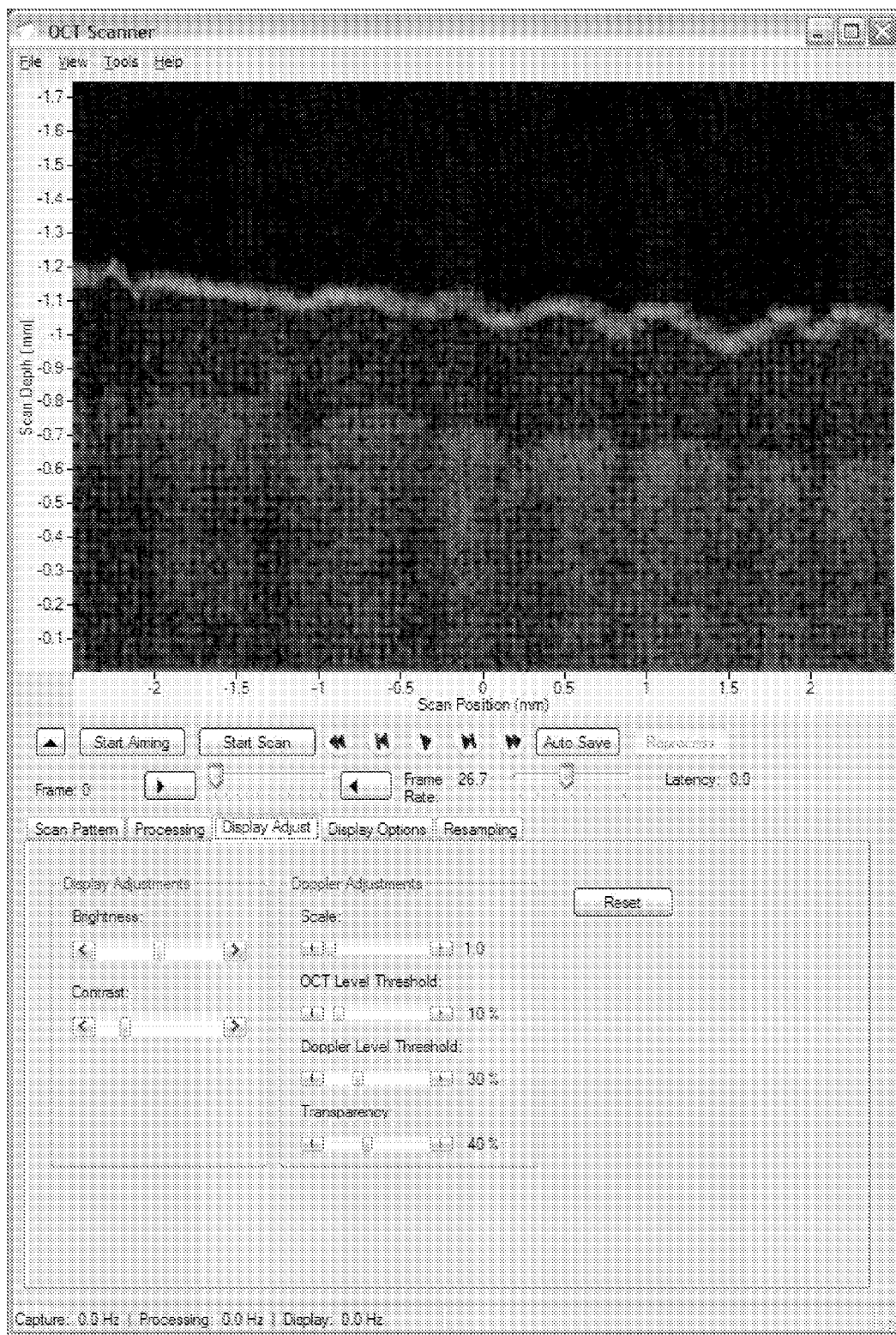
FIG. 11 is a screen shot illustrating the main window, display adjust tab according to some embodiments of the present invention.
Figure 12:
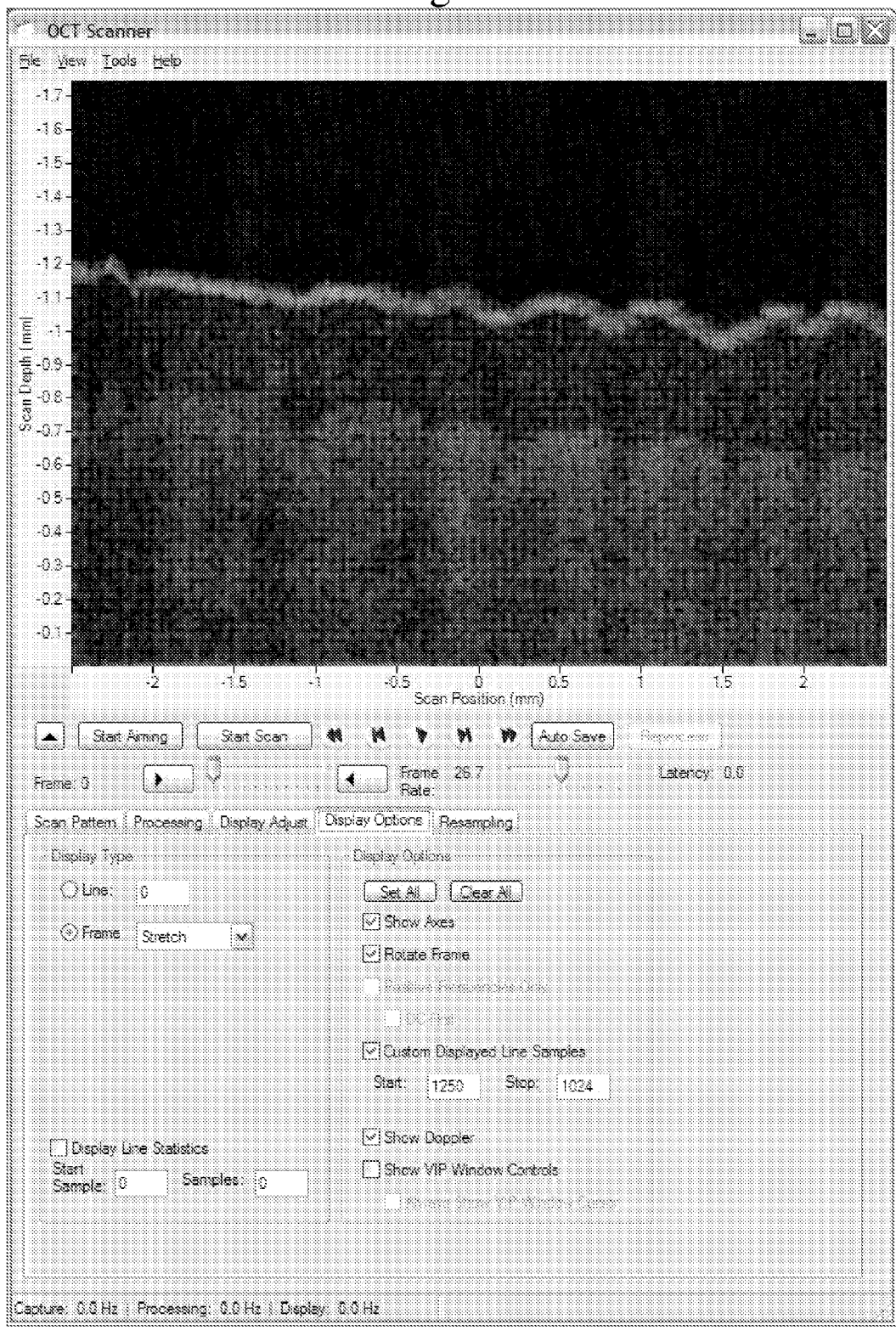
FIG. 12 is a screen shot illustrating the main window, display options tab according to some embodiments of the present invention.
Figure 13:
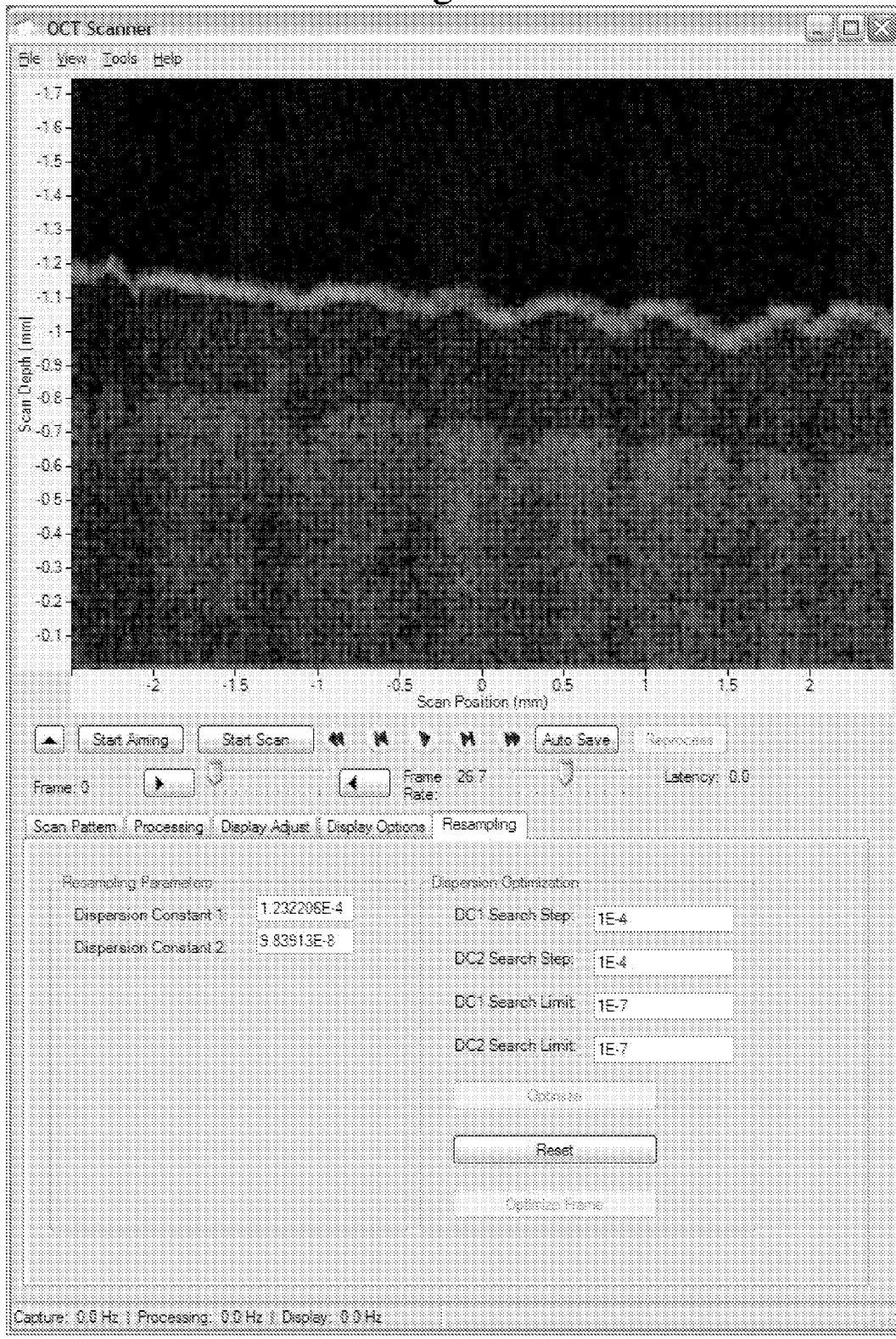
FIG. 13 is a screen shot illustrating the main window, resampling tab according to some embodiments of the present invention.
Figure 14:
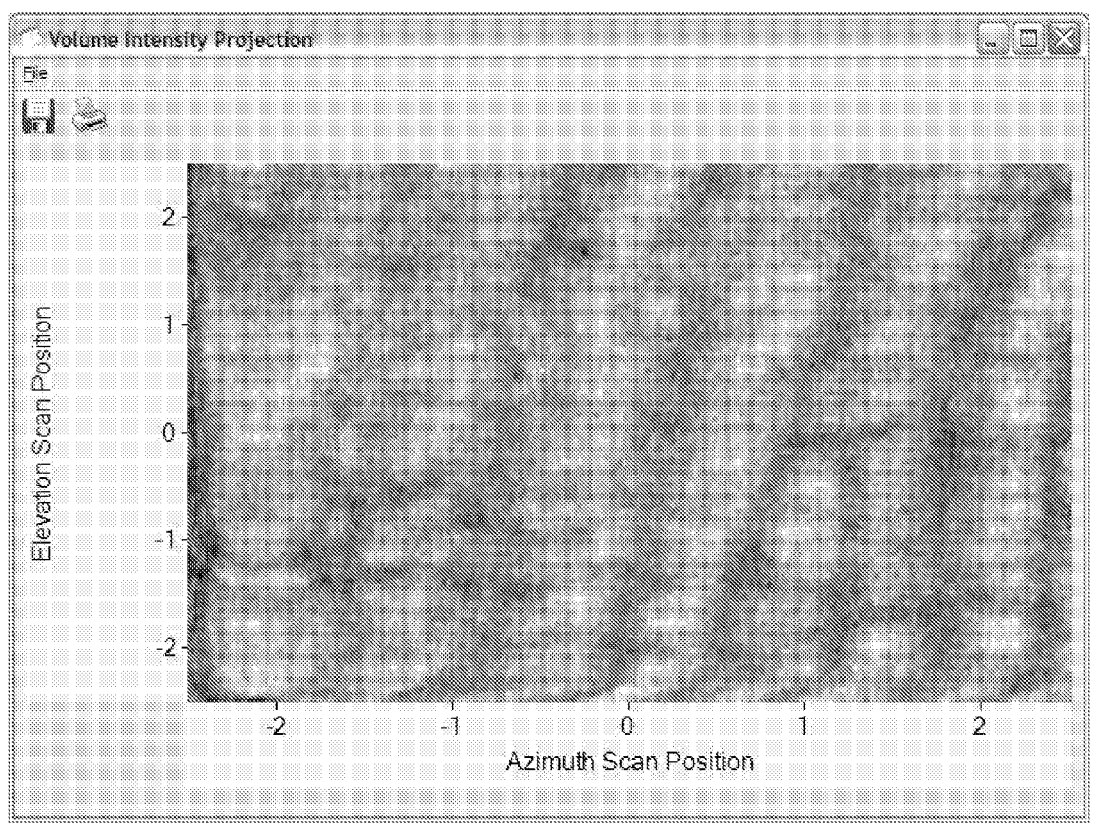
FIG. 14 is a screen shot illustrating a Volume Intensity Projection Window to some embodiments of the present invention.
Figure 15:
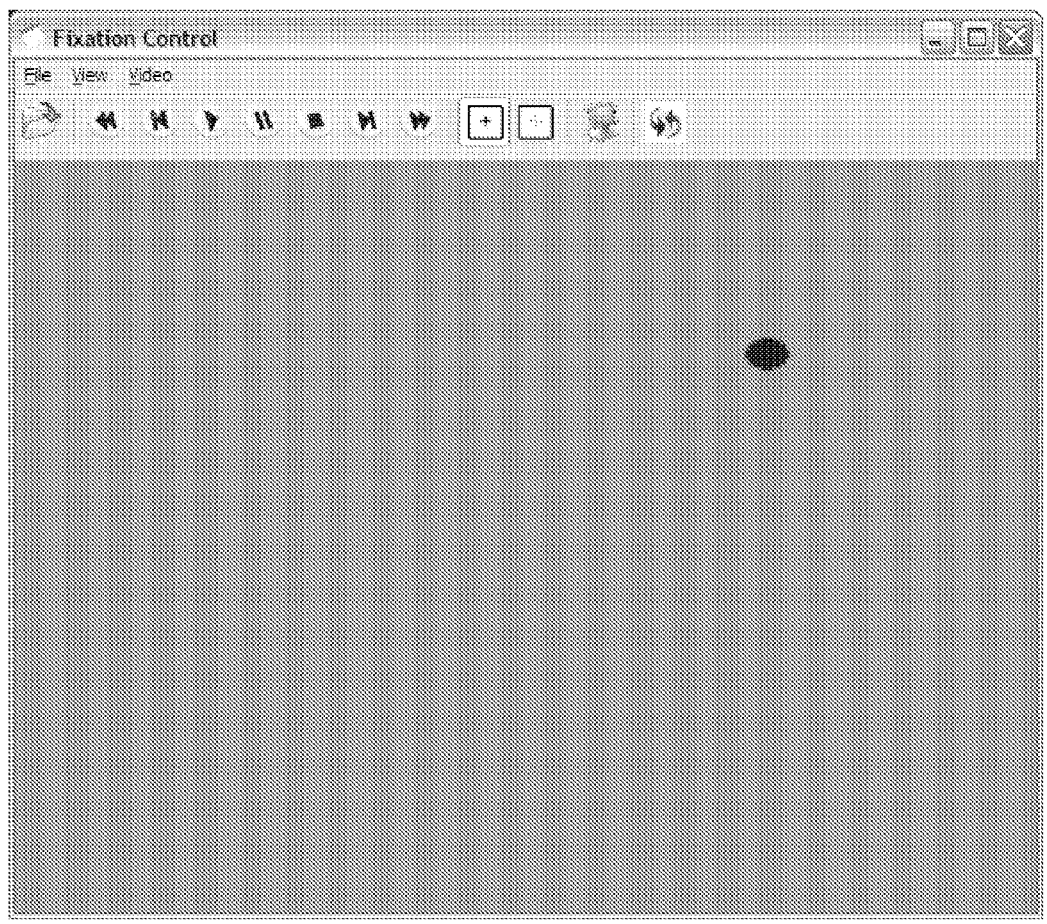
FIG. 15 is a screen shot illustrating a Fixation Control Window according to some embodiments of the present invention.
Figure 16:
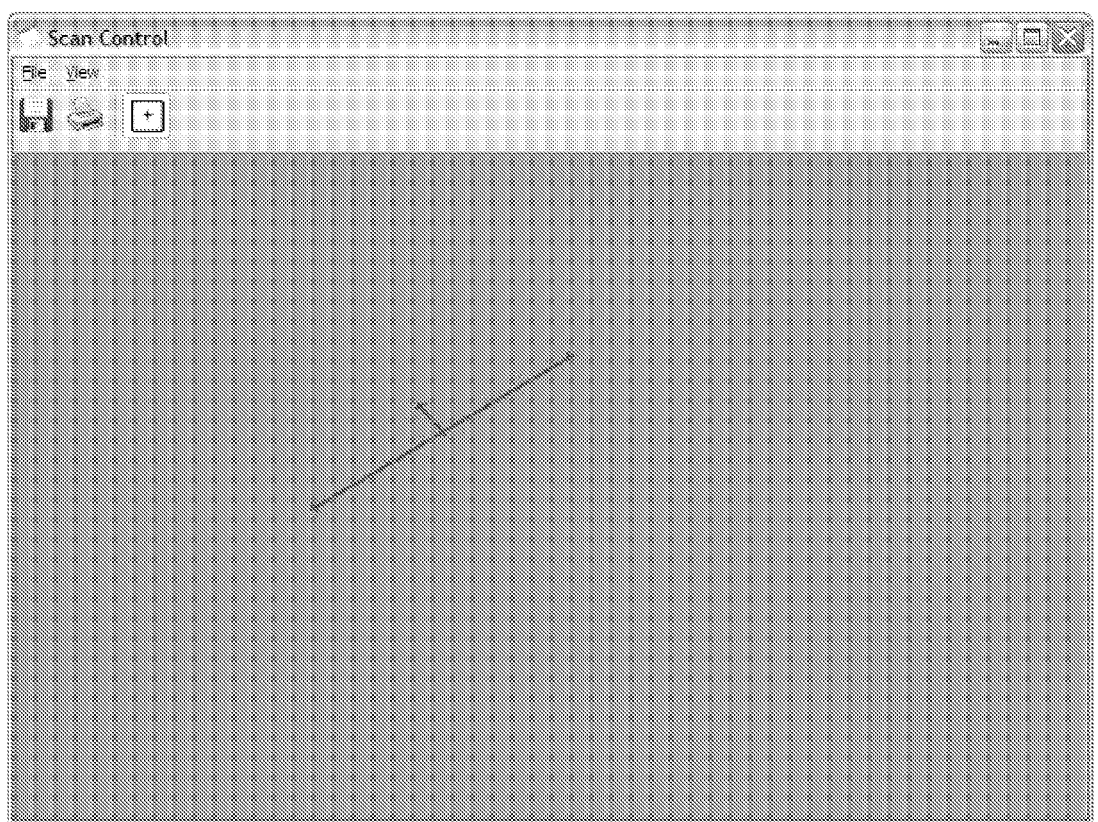
FIG. 16 is a screen shot illustrating a Control Window according to some embodiments of the present invention.
Figure 17:
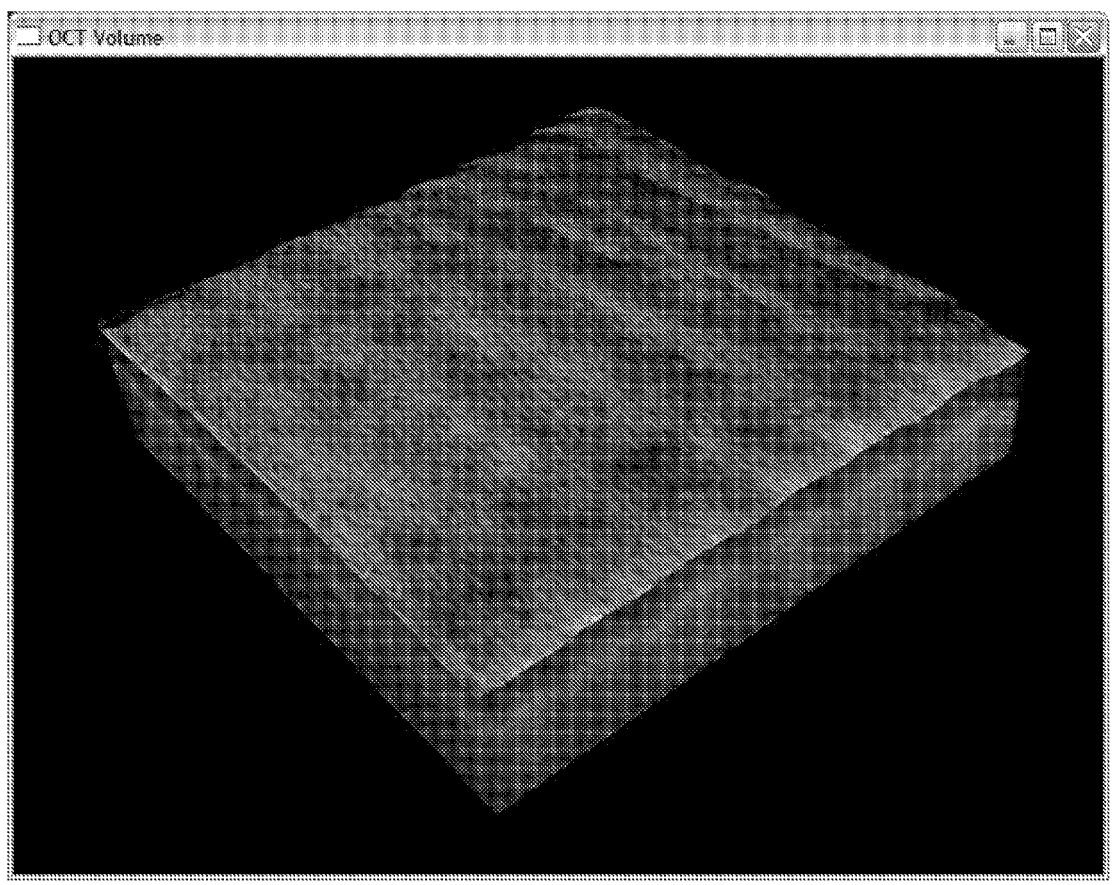
FIG. 17 is a screen shot illustrating a 3D volume display window according to some embodiments of the present invention.
Figure 18:
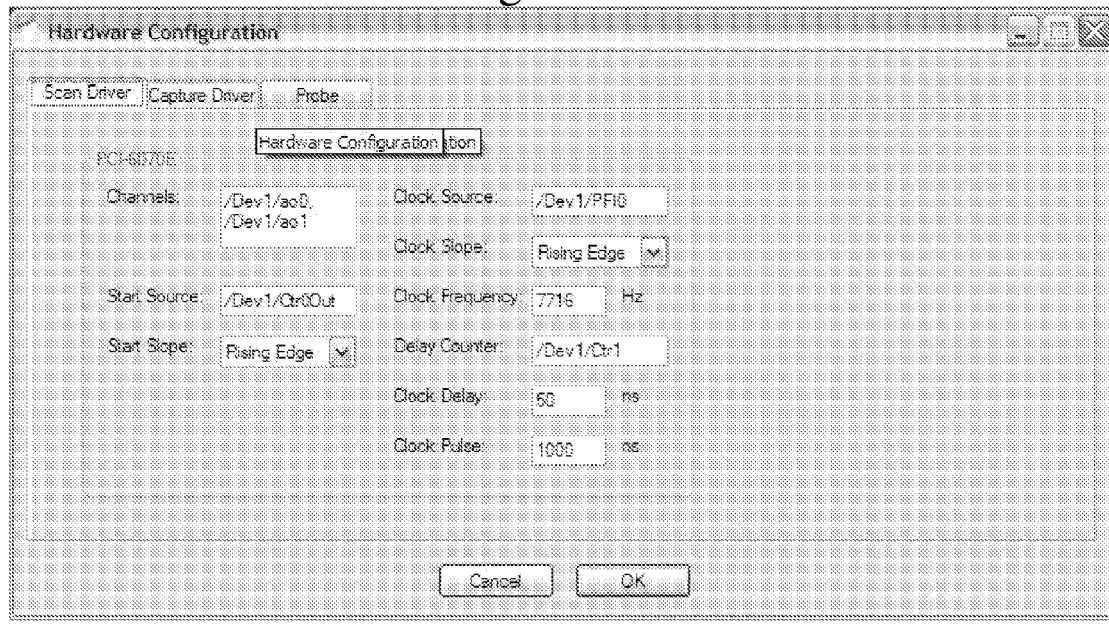
FIG. 18 is a screen shot illustrating Hardware Dialog, Scan tab according to some embodiments of the present invention.
Figure 19:
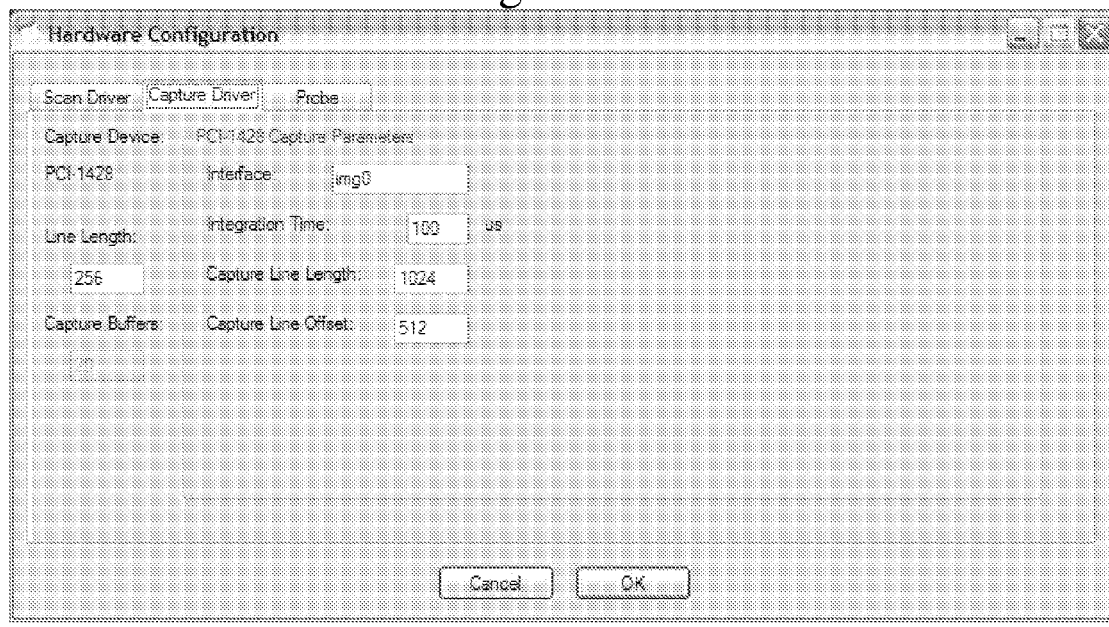
FIG. 19 is a screen shot illustrating Hardware Window, capture tab according to some embodiments of the present invention.

Referring now to the flowchart of FIG. 8, operations for processing data obtained using an FDOCT system begin at block 803 by acquiring an image using FDOCT. The raw frequency domain data associated with the acquired image in a data archive is stored (813). The stored frequency domain data is processed to provide improved images acquired using FDOCT (block 823).

In some embodiments of the present invention, processing may include applying algorithms to the stored raw frequency domain data during at least one step of a processing pipeline to provide improved images acquired using FDOCT. Processing may further include applying FFT algorithms to the stored raw frequency domain data; applying windowing functions to the FFT algorithms; applying filtering functions to the FFT algorithms; applying dispersion compensation algorithms to the stored raw frequency domain data; applying spectral calibration algorithms to the stored raw frequency domain data; and/or applying averaging algorithms to the stored raw frequency domain data.

In some embodiments of the present invention, applying averaging algorithms may include applying averaging algorithms that are directly accessible by a user. The averaging algorithms may include line averaging including acquiring a plurality of depth lines in one lateral location for averaging, moving to a next lateral location, and averaging the plurality of depth lines for each location; moving window averaging including acquiring a lateral scan including a plurality of depth lines and averaging a user-specified contiguous subset of adjacent depth lines; and frame registration averaging including registration of m complete lateral scans of n depth lines to each other and averaging the m complete lateral scans of the n depth lines.

In some embodiments of the present invention, the space domain data may be stored along with the raw frequency domain data. As discussed above, some embodiments of the present invention provide for storage and archiving of the frequency domain data. A metadata file may be associated with the frequency domain data to allow on-demand processing into space domain data. Some embodiments of the present invention may create a client-server architecture whereby the frequency-domain data and metadata may be stored away from the imaging hardware and/or the point of analysis, and may be processed into space domain data remotely.

Frequency domain metadata may include scan operation, spectral calibrations, and phase rules that allow for on-demand spectral filtering and phase operations. The frequency domain metadata may further include subject specific information as necessary to unambiguously tie the data to the subject. Furthermore, the frequency domain metadata may include subject specific information as necessary to unambiguously tie the data to the subject while retaining privacy as required by law.

Some embodiments of the present invention may provide very fast or virtually immediate processing from the frequency domain to the space domain. Relevant information for this class of processing may be included in the metadata. A sequence of one or more frequency domain processing steps may be user-defined to perform specific transform operations to extract user-desired information or generate user-desired images.

The frequency domain processing steps may be recorded as metadata, such that the so generated data can be recreated from the original frequency domain data, the original metadata, and the operationally defined metadata.

In some embodiments of the present invention, the storage of image data may include the archival frequency domain data, the original archival metadata sets, operational metadata sets that are sufficient to recreate any space domain image so processed, and any images created through the user-defined operations as specified for storage by the user.

It will be understood that client-side or web-based software may be able to process any of this available data without reference to or connection with the original imaging hardware.

Thus, in some embodiments of the present invention, the raw Fourier-domain data and its associated calibration tables may be the primary archived information set stored in the data archive for FDOCT in order to provide the most reliable and reusable historical record of the imaged subject.

In some embodiments of the present invention, methods are applied to provide real-time control and processing of the Fourier-to-spatial domain data by efficient control of processor functionality. For example, some embodiments of the present invention use multithreading techniques to decrease processing times. As used herein, "multithreading" refers to efficiently splitting and pipelining the processing steps involved in the image processing to increase the image throughput and reduce image latency.

Figure 4:
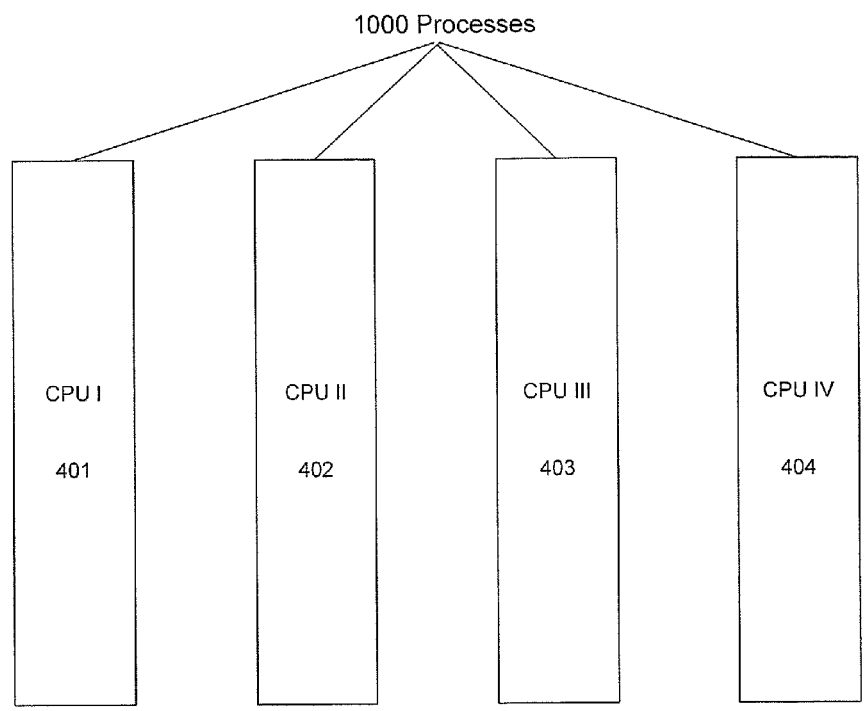
FIG. 4 is a block diagram illustrating multithreading according to some embodiments of the present invention.

For example, as illustrated in FIG. 4, 1000 FFT processes 400 may be split among multiple CPUs, for example, four CPUs 401-404, so that the processing is done in parallel to decrease overall processing time. Each FFT process 400 must be done by a single CPU. However, if a particular image requires, for example, 1000 FFT processes 400, 250 processes may be allocated to each CPU 401, 402, 403 and 404, which may cut the processing time to 25% of processing times provided by a single CPU.

Although embodiments of the present invention illustrates that the processing is divided among 4 CPUs, the processing may be divided among three or less or more than four CPUs without departing from the scope of the present invention.

As discussed above, OCT engines according to some embodiments of the present invention generate 20,000 or more lines of spectral data each containing 2048 or more samples per second. This data may go through a large number of complex processing steps in order to produce spatial data representing the reflected light in the subject at each point in depth. This processing is typically far beyond the capabilities of the fastest single processor computers available today.

Thus, in order to take advantage of the multiple-processor computers available, the processing steps in some embodiments of the present invention are organized as a multi-threaded pipeline and divided among the available processors as illustrated in FIG. 4.

Figure 22:
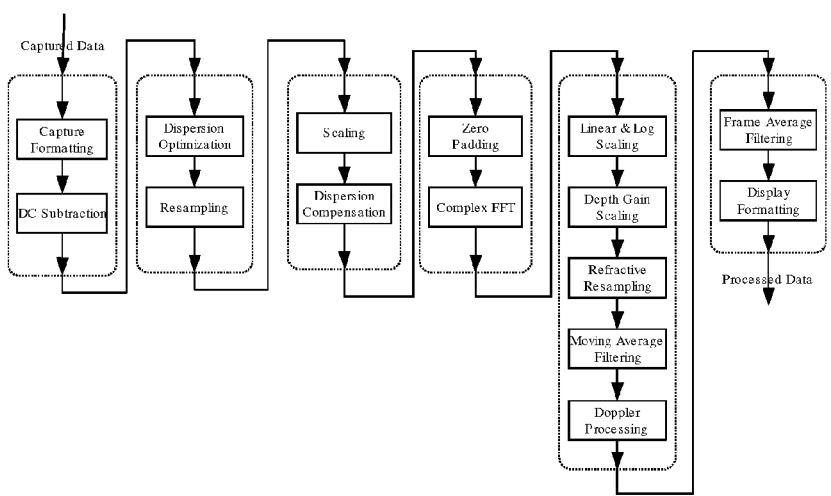
FIG. 22 is a flow diagram illustrating division of the processing steps among the pipeline stages according to some embodiments of the present invention.

A block diagram illustrating organization of processing steps as a multi-threaded pipeline and divided among the available processors and a flow diagram illustrating division of the processing steps among the pipeline stages according to some embodiments of the present invention are illustrated in FIGS. 21 and 22, respectively.

Operations of the display module 224 will now be discussed. In some embodiments of the present invention, certain image processing features may be simplified for the user. For example, in some embodiments of the present invention, axial slices (c-scans) of volumetric data may be displayed and controlled without reverting to a volumetric rendering engine. A Volume Intensity Projection (VIP) or Summed Voxel Projection, may be displayed by displaying a weighted sum of the depth-dependent data over all or a subset of the lateral scan range, where the weighting may be uniform over the entire depth, uniform over a selected depth, or non-uniform over all or a selected depth.

In some embodiments of the present invention, the weighting function is controlled simply by the user through the access of two or more control items that indicate, for example, on a cross-sectional subset of the data, the center position of the summed data and the range of the summed data, where the range may be the boundaries of a uniform sum, or may be a parametric representation of a non-uniform sum as, for example, the standard deviation of Gaussian weighting factor applied to the summation.

As discussed above with respect to FIG. 3, some embodiments of the present invention provide tools that may allow modification of the image in real time. In particular, control items may be applied to modifying the center or range in essentially real-time for immediate feedback to the user. The control items may include a selection tool for setting the weighting function to be applied to the summation.

VIPs are discussed in commonly assigned United States Patent Publication No. 2007-0025642, filed Jul. 31, 2006, entitled Methods, Systems And Computer Program Products For Analyzing Three Dimensional Data Sets Obtained From A Sample, the contents of which is hereby incorporated herein by reference as if set forth in its entirety.

FIGS. 9 through 20 illustrate exemplary screen shots according to some embodiments of the present invention.

In the drawings and specification, there have been disclosed embodiments of the invention and, although specific terms are employed, they are used in a generic and descriptive sense only and not for purposes of limitation, the scope of the invention being set forth in the following claims.

That which is claimed is:

1. A Fourier Domain Optical Coherence Tomography (FDOCT) image processing system, the system comprising:
   a display;
   a processor configured to transform a frequency domain spectral interferogram into a spatial domain image using both subject-specific metadata and hardware-specific metadata; and
   a storage module configured to store the frequency domain spectral interferogram;
   wherein the subject-specific metadata contains information associated with one of a subject and a class of subjects;
   wherein the hardware-specific metadata contains information associated with one of a hardware configuration or class of hardware configurations; and
   wherein the display is configured to display spatial domain image data.

2. The system of claim 1, wherein the subject-specific metadata includes dispersion correction parameters.

3. The system of claim 2, wherein the processor is further configured to apply the dispersion correction parameters in the transformation of the frequency domain spectral interferogram to the spatial domain image.

4. The system of claim 3, wherein the processor is further configured to:
   optimize dispersion correction parameters; and
   reprocess the frequency domain spectral interferogram using the improved optimized dispersion correction parameters to provide an optimized spatial domain image.

5. The system of claim 1, wherein the hardware-specific metadata includes spectral calibration data for correlating frequency domain data elements to corresponding optical frequencies.

6. The system of claim 5, wherein the processor is further configured to apply the spectral calibration data in the transformation of the frequency domain spectral interferogram to the spatial domain image.

7. The system of claim 1, wherein the processor is further configured to reduce image speckle using time-separated averaging of spatial domain data.

8. The system of claim 1, wherein the processor is further configured to apply a spectral filter to the frequency domain spectral interferogram prior to transforming the frequency domain data to the spatial domain image.

9. The system of claim 8, wherein the processor is further configured to compare the spatial domain image derived from the application of a first spectral filter to the spatial domain image derived from the application of a second spectral filter.

10. A method of processing a Fourier Domain Optical Coherence Tomography (FDOCT) image, the method comprising:
    retrieving a frequency domain spectral interferogram from a non-transitory storage module;
    retrieving subject-specific metadata containing information associated with one of a subject and a class of subjects;
    retrieving hardware-specific metadata containing information associated with one of a hardware configuration and a class of hardware configurations;
    processing the frequency domain spectral interferogram into a spatial domain image using the retrieved subject-specific and hardware-specific metadata,
    wherein at least one of the retrieving a frequency domain spectral interferogram, retrieving subject-specific metadata, retrieving hardware-specific metadata and processing is performed by at least one processor in an Optical Coherence Tomography imaging processing system.

11. The method of claim 10, wherein processing further comprises applying dispersion correction parameters to the frequency domain spectral interferogram to derive the spatial domain image.

12. The method of claim 10, wherein processing further comprises:
    optimizing dispersion correction parameters; and
    reprocessing the frequency domain spectral interferogram using the optimized dispersion correction parameters to provide an optimized spatial domain image.

13. The method of claim 10, wherein the processing further comprises averaging of spatial domain data elements acquired at approximately a same location but separated in time to introduce fluctuations in phase to reduce speckle on averaging.

14. The method of claim 13, further comprising collecting a sequential series of two-dimensional frames of data and averaging frames of data to provide the time separation.

15. The method of claim 10, wherein processing further comprises applying a spectral filter to the frequency domain data spectral interferogram to transform the frequency domain spectral interferogram to the spatial domain image.

16. The method of claim 15, wherein processing further comprises comparing the spatial domain image derived from the application of a first spectral filter to the spatial domain image derived from the application of a second spectral filter.

* * * * *

UNITED STATES PATENT AND TRADEMARK OFFICE
CERTIFICATE OF CORRECTION

PATENT NO. : 8,401,257 B2  
APPLICATION NO. : 12/016352  
DATED : March 19, 2013  
INVENTOR(S) : Izatt et al.

Page 1 of 1

It is certified that error appears in the above-identified patent and that said Letters Patent is hereby corrected as shown below:

In the Specification:

Column 15, Line 37: Please correct "in—9526-11."
to read -- in United States Patent No. 7,719,692 to *Izatt et al.*, issued May 18, 2010, entitled *Methods, Systems and Computer Program Products for Optical Coherence Tomography (OCT) Using Automatic Dispersion Compensation.* --

Signed and Sealed this
Fifteenth Day of April, 2014

Michelle K. Lee
*Deputy Director of the United States Patent and Trademark Office*